US006281680B1

(12) United States Patent
Matthews et al.

(10) Patent No.: US 6,281,680 B1
(45) Date of Patent: *Aug. 28, 2001

(54) METHOD AND APPARATUS FOR DISTINGUISHING SYNTHETIC DIAMONDS FROM NATURAL DIAMONDS

(75) Inventors: Marion Matthews, 8461 Vereda Del Padre, Goleta, CA (US) 93117; Charles R. Perry, Goleta, CA (US)

(73) Assignee: Marion Matthews, Goleta, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/694,877

(22) Filed: Aug. 9, 1996

Related U.S. Application Data

(63) Continuation-in-part of application No. 08/342,840, filed on Nov. 21, 1994, now Pat. No. 5,559,436.

(51) Int. Cl.[7] ............................ G01R 33/12; G01N 27/72
(52) U.S. Cl. ......................... 324/236; 324/234; 324/228
(58) Field of Search .................................. 324/228, 234, 324/236, 327, 377, 239, 233; 327/39–49; 356/30; 331/65

(56) References Cited

U.S. PATENT DOCUMENTS

| 3,808,524 | 4/1974 | Tarassoff et al. ..................... 324/236 |
| 3,858,979 | 1/1975 | Elbe ....................................... 356/30 |
| 4,075,563 | * | 2/1978 | Battle .................................. 324/236 |

(List continued on next page.)

FOREIGN PATENT DOCUMENTS 617212    11/1927   (FR) .
714263A   *  2/1980  (SU) .

OTHER PUBLICATIONS

Minster, David, "The Separation of Natural from Synthetic Diamonds Using the Barkhausen Effect", *J. Gemm.* 20, 7/8, pp. 458–459 (1987).
Shigley, James E. et al., "The Gemological Properties of the De Beers Gem–Quality Synthetic Diamonds", *Gems & Gemology*, pp. 187–206, Winter 1987.

(List continued on next page.)

*Primary Examiner*—Jay Patidar
(74) *Attorney, Agent, or Firm*—Chrisie, Parker & Hale, LLP

(57) ABSTRACT

A method and apparatus are provided for distinguishing synthetic diamonds from natural diamonds by detecting the effect the synthetic diamonds have on a magnetic field. A counter can be provided for measuring counting transitions of an oscillator having an inductor in a frequency determining circuit. The inductor has a port therein for admitting a sample diamond for testing. First, the oscillations are up counted over a precise time interval with no sample present, and then a sample diamond is placed into coupled proximity with the inductor to change the frequency of the circuit by an amount related to the quantity of ferromagnetic material in the sample diamond. Thereafter, a down count is performed for the oscillations with the sample diamond in place over a second time interval equal to the first interval. The difference in the up counts and the down counts is determined and displayed in a digital readout as a measure of the degree of likelihood of the sample being synthetic. Alternatively, a sample diamond can be placed in coupled proximity to a coil in a tuned circuit. A resultant change in the output amplitude of the tuned circuit is detected from which a display is generated indicating the degree of likelihood of the sample being synthetic. A sample diamond can also be rotated in a magnetic field. A signal induced in a coil is detected from which an indication of the degree of likelihood of the sample being synthetic is displayed.

18 Claims, 18 Drawing Sheets

U.S. PATENT DOCUMENTS

| | | | |
|---|---|---|---|
| 4,125,770 | | 11/1978 | Lang ........................................ 378/74 |
| 4,131,848 | * | 12/1978 | Battle ...................................... 324/236 |
| 4,255,962 | | 3/1981 | Ashman ................................. 73/15 A |
| 4,291,975 | | 9/1981 | Raccah .................................... 356/30 |
| 4,364,677 | | 12/1982 | Ashman .................................. 374/44 |
| 4,461,568 | | 7/1984 | Welbourn et al. ...................... 356/30 |
| 4,488,821 | | 12/1984 | Wenckus ................................. 374/44 |
| 4,523,467 | * | 6/1985 | Diederichs et al. ................... 73/573 |
| 4,616,939 | | 10/1986 | Gitlis ....................................... 374/44 |
| 4,678,994 | | 7/1987 | Davies .................................... 324/236 |
| 4,835,471 | | 5/1989 | Kutilin ................................... 324/236 |
| 5,064,281 | | 11/1991 | Davis ...................................... 356/30 |
| 5,143,212 | | 9/1992 | Roberts et al. ....................... 206/223 |
| B1 4,255,962 | | 1/1983 | Ashman ................................. 374/44 |

OTHER PUBLICATIONS

Shigley, James E. et al., "The Gemological Properties of the Sumitomo Gem–Quality Synthetic Yellow Diamonds", *Gems & Gemology*, pp. 192–208, Winter 1986.

Gordon, Derck A., "Determination of the Magnetic Anisotropy of Single Crystals from Magnetic Torques Measured with Quartz Fibers", *The Review of Scientific Instruments*, vol. 29, No. 11, pp. 929–934, Nov. 1958.

* cited by examiner

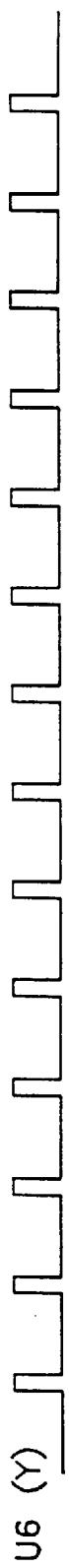
FIG. 4A U6 (Y)
FIG. 4B U6 (Y+D)
FIG. 4C U2A (Q)
FIG. 4D U2B (Q)
FIG. 4E REF. CLOCK

METHOD AND APPARATUS FOR DISTINGUISHING SYNTHETIC DIAMONDS FROM NATURAL DIAMONDS

CROSS REFERENCE TO RELATED APPLICATIONS

This is a continuation-in-part of application Ser. No. 08/342,840 filed Nov. 21, 1994 and U.S. Pat. No. 5,559,456 (as amended).

FIELD OF THE INVENTION

This invention relates to the screening of diamond gemstones so as to distinguish and detect synthetic diamonds from natural diamonds. More particularly, the invention relates to a method and apparatus for the rapid screening of diamond gemstones to determine the need for further investigation by identifying those likely to be synthetic. The invention produces a negative response for natural diamonds but reacts to the magnetic properties of synthetic diamonds to provide an indicator thereof.

BACKGROUND OF THE INVENTION

With the advent of gemstone quality synthetic diamonds the need has arisen for a rapid screening system available and affordable for the local jeweler to establish with reasonable probability whether a given diamond gemstone is natural or synthetic.

Existing systems for detection of synthetic diamond gemstones are summarized in the article Shigley et al., "Sumitomo Synthetic Diamonds", *Gems and Gemology*, Winter 1986, pages 192–208. As there indicated the various properties of diamonds and particularly those that distinguish natural from synthetic stones are compared. Testing procedures were set forth which included color, (which may involve spectroscopy examination), fluorescence, electrical conductivity, thermal conductivity, specific gravity, microscope inspection, reaction to polarized light, and magnetism. As to the latter, magnetism, the test procedure involved gross attraction of the tested diamond to a magnet. However, it was found that only one of the tested synthetic diamonds was attracted so that the reliability of a test as there proposed was found inadequate.

A subsequently published article by Shigley et. al., "Gemological Properties of the De Beers Gem Quality Synthetic Diamonds", *Gems and Gemology*, Winter 1987, pages 187–206, repeated the previous work and investigation as applied to the De Beers synthetic diamond product. In addition to the tests earlier performed, the last publication also indicates that a test was conducted with catholuminescence and specific gravity investigations as well as chemical analysis of inclusions. As to the magnetic behavior it was noted that natural diamonds are only weakly magnetic if at all and that synthetic diamonds were believed to vary from strongly magnetic to non-magnetic. Accordingly, these studies concluded that magnetic investigation of synthetic diamond gemstones was not useful for identification. They further state that they foresaw difficulties in separating natural from synthetic colorless diamonds using any other conventional gemological technique.

In addition, various techniques have been used to determine the content of magnetic compounds such as magnetite and pyrhotite in ore samples. For example, U.S. Pat. No. 3,808,524 (Tarassoff et al., "APPARATUS FOR DETERMINING THE AMOUNT OF MAGNETIC MATERIAL IN A SAMPLE") discloses an apparatus that determines the amount of a magnetic compound in an ore sample by inserting the sample into a coil of an oscillator and detecting the change in the oscillating frequency of the oscillator.

Conventional teachings in the synthetic diamond art indicate that synthetic diamond screening tests based on magnetic qualities of the diamonds are inadequate. Thus, these teachings suggest that methods such as those disclosed in Tarassoff would probably be ineffective. Accordingly, a need exists for a relatively easy to use and inexpensive method and apparatus for distinguishing between synthetic diamonds and natural diamonds.

SUMMARY OF THE INVENTION AND OBJECTS

In general, it is an object of the present invention to provide a method and apparatus for distinguishing synthetic diamonds from natural diamonds which will overcome the above limitations and disadvantages.

It is a further object of the invention to provide a method and apparatus of the above character based on a test for magnetic susceptibility of the stone.

It is known that natural diamonds exhibit very little if any magnetic behavior which could form the basis of their evaluation. However, synthetic diamonds have been found to contain magnetic inclusions inherent from the process from which they are made. Even though these inclusions can be quite small they are nevertheless found to exist in all synthetic diamonds that have been investigated whether or not detectable by the gross magnetic attraction methods mentioned in the literature. Even the clearest of synthetic stones contain ferrous material presumably more evenly distributed at the molecular level.

The present invention is based upon the realization that, contrary to conventional teachings in the synthetic diamond art, synthetic diamonds can be distinguished from natural diamonds by testing the magnetic properties of the diamonds. Specifically, trace amounts of iron are detected in synthetic diamonds using sufficiently sensitive instruments capable of detecting the effect the trace amounts of iron have on a magnetic field.

In a first embodiment, the present invention is predicated upon the realization that, given a suitably sensitive and appropriate instrumentation, it is possible to screen synthetic diamond gemstone from natural diamond gemstones by placing the stone under test into the core of an inductance in a linear oscillator circuit in which the magnetic character of the synthetic diamond changes the inductance and affects the frequency of the oscillating circuit in a way that a difference count can be obtained over a precisely repeatable interval for the condition of no sample present, compared to that when the sample is present, by an extremely sensitive but stable counting circuit. It is found that a reliable screening method can be based on this concept.

Generally, the invention provides a counter for measuring or counting transitions of an oscillator having an inductor in a frequency determining circuit. The inductor is in at least in part air cored, being wound around a core form having an opening therein for admitting a sample into the inductor core for testing. The method calls for upcounting the oscillations of the oscillator over a precisely repeatable time interval with no sample present and thereafter selectively placing an unknown sample diamond stone into coupled proximity or within the core of the inductor to change the oscillator frequency by an amount related to the ferromagnetic material contained therein. At that point the system is signaled to down-count the oscillations, subtracting the same from the up-count over a second time interval precisely equal to the first interval. The difference in counts is determined and displayed on a digital readout as a measure of the degree of likelihood that the sample under test is synthetic.

In a second embodiment, the diamond sample is positioned near a coil of a tuned circuit. When the diamond sample is a synthetic diamond, the iron in the diamond sample alters the parameters of the coil (e.g., the "Q" of the coil) which, in turn, changes the amplitude of the output signal of the tuned circuit. The change in amplitude is detected and displayed to indicate the degree of likelihood that the sample under test is synthetic.

The second embodiment typically provides an even more sensitive screening device than the first embodiment. First, the second embodiment uses a fixed frequency oscillator. As a result, its sensitivity is not affected by frequency drift as much as the first embodiment. Second, using tuned circuits and a differential amplifier, this embodiment can detect very small changes in the Q of the coil. Consequently, this embodiment provides a very sensitive screening apparatus.

In a third embodiment, the diamond sample is moved within a magnetic field. When the diamond sample is a synthetic diamond, iron inclusions within the diamond disturb the magnetic field. This disturbance generates a signal that is detected by the screening apparatus. This signal is amplified and processed to generate a display indicating the degree of likelihood that the sample under test is synthetic.

Typically, this embodiment provides an even more sensitive screening device than the embodiments discussed above. Consequently, this embodiment provides a very effective yet relatively simple screening device.

BRIEF DESCRIPTION OF THE DRAWINGS

These and other features and objects of the invention will become apparent from the following description and claims, when taken with the accompanying drawings, wherein similar reference characters refer to similar elements throughout and in which:

FIGS. 4A–4E is a set of timing signal graphs depicting the operation of the reference oscillator of FIG. 3;

DETAILED DESCRIPTION OF THE PREFERRED EMBODIMENTS

Figure 11:
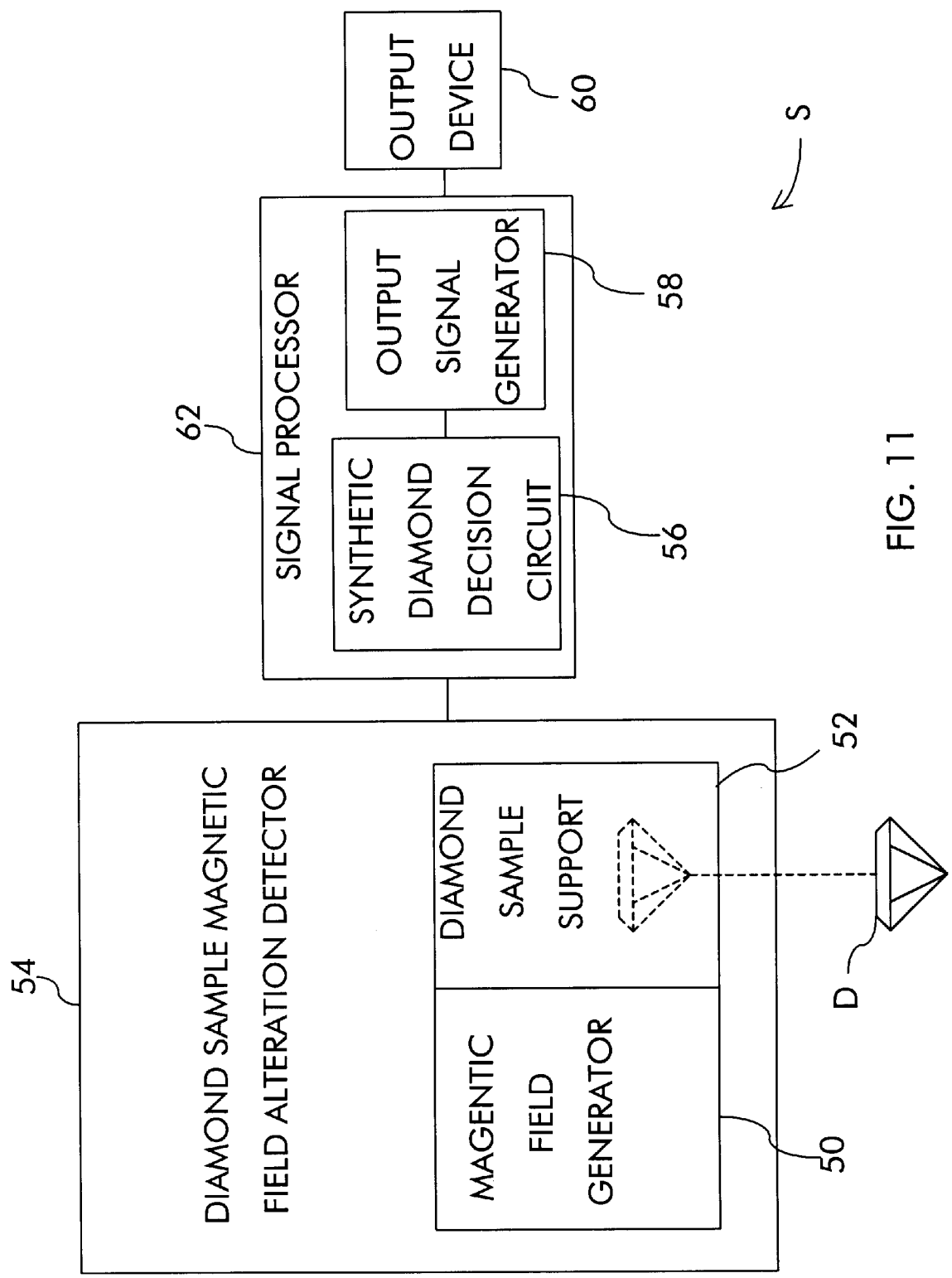
FIG. 11 is a generalized block diagram of a synthetic diamond screening device constructed according to the present invention.

Referring to FIG. 11, a block diagram illustrates a synthetic diamond screening device S according to the present invention. The screening device S identifies a synthetic diamond by detecting magnetically sensitive inclusions in the synthetic diamond. The inclusions result from the process of producing a synthetic diamond by growing synthetic diamond crystals in an iron-based flux. The presence of the flux causes iron particles to become entrapped in the crystal during the growth process.

The screening device S detects inclusions in a diamond sample by detecting the effect the inclusions have on a magnetic field. A magnetic field generator 50 (FIG. 11, left) produces a magnetic field (not shown) and a diamond sample support 52 positions a diamond sample D in the magnetic field. A diamond sample magnetic field alteration detector 54 detects the effect the diamond sample D has on the magnetic field and a synthetic diamond decision circuit 56 generates a signal which indicates the probability that the diamond sample D is synthetic. An output signal generator 58 processes this signal to generate an output signal that drives an output device 60. The output device 60 provides a visual indication of whether the diamond sample D is a synthetic diamond or a natural diamond.

Three embodiments of the present invention are presented. In a first embodiment, a diamond sample is placed in a magnetic field generated by a coil of an oscillator. The presence of ferrous material (i.e., iron) in the diamond sample changes the effective inductance of the coil which, in turn, changes the operating frequency of the oscillator. The apparatus determines the probability that the sample is synthetic based on the change in the operating frequency. In a second embodiment, a diamond sample is placed in a magnetic field generated by a coil of a tuned circuit. In this embodiment, a change in the Q of the coil changes the amplitude of the output signal of the tuned circuit. The apparatus determines the probability that the sample is synthetic based on this change in amplitude. In a third embodiment, a diamond sample is rotated in a magnetic field. The presence of ferrous material in the diamond sample disturbs the magnetic field and generates a signal in a magnetic head. The apparatus determines the probability that the sample is synthetic based on this signal.

Figure 1:
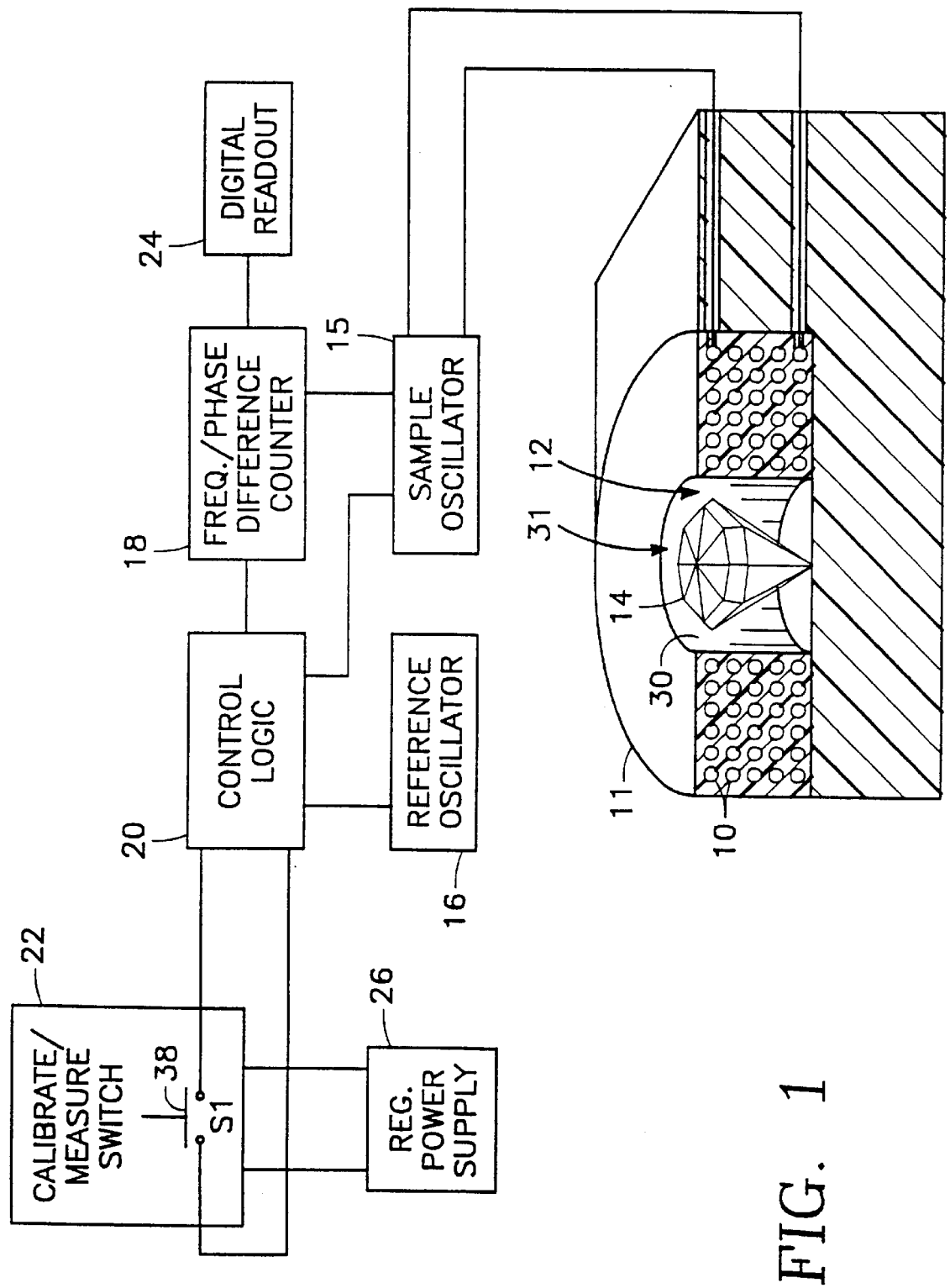
FIG. 1 is a block diagram of a detection apparatus constructed in accordance with a first embodiment of the present invention.

Referring to FIG. 1, the first embodiment of the present invention screens a diamond sample by detecting a change in the operating frequency of an oscillator that results from placing the sample in the frequency determining coil of the oscillator. A sample oscillator 15 and its associated coil 10 substantially provide the functionality of the magnetic field alteration detector 54 of FIG. 11. The remaining components of FIG. 1 substantially provide the functionality of the signal processor 62 and the output device 60 of FIG. 11.

A sample receiving coil 10 mounted with one end 12 opening through the top of a case into which the operator places the stone 14 to be tested. Coil 10 forms an inductance which is part of a frequency determining circuit configuration of a free-running sample oscillator 15. Current flowing through the coil 10 generates a magnetic field around the coil 10. Iron in the stone 14 interacts with the magnetic field and changes the inductance of the inductive circuit which includes the coil 10 and the stone 14. Because the inductive circuit is part of the frequency determining circuit of the oscillator, the change in the inductance of the inductive circuit changes the operating frequency of the oscillator.

The apparatus of FIG. 1 processes the change in the operating frequency of the oscillator to provide a visual indication on a digital readout (FIG. 1, right) of the probability that the stone 14 is a synthetic diamond. A stable reference oscillator 16 clocks a counter 18 and control logic 20 controlled by a user calibrate/measure switch 22 to establish an up-count reference interval initiated by the operator before inserting the stone into coil 10. This interval is exactly matched after an unknown stone is placed for test and the operator gives the start test signal by releasing the switch 22.

During each of the reference interval and the test interval, the number of transitions of the sample oscillator is determined, and the down-counts of the latter are subtracted from the up-counts of the former to obtain a difference count which is displayed in a suitable readout. When the stone is natural, it contains no ferrous material, and the up-counts and down-counts match so that the output displayed is very low or zero. But, when the stone contains ferrous material, either in inclusions or distributed at the molecular level, the frequency of the sample oscillator is changed, so that the down-count will not equal the up-count. The difference of the counts is then displayed in digital readout 24 which signals the likelihood of a synthetic stone whenever the value exceeds a predetermined threshold level. The apparatus uses a stable voltage reference supplied by a regulated power supply 26 which can be connected to AC mains.

Sample Oscillator Circuit 15

Figure 2:
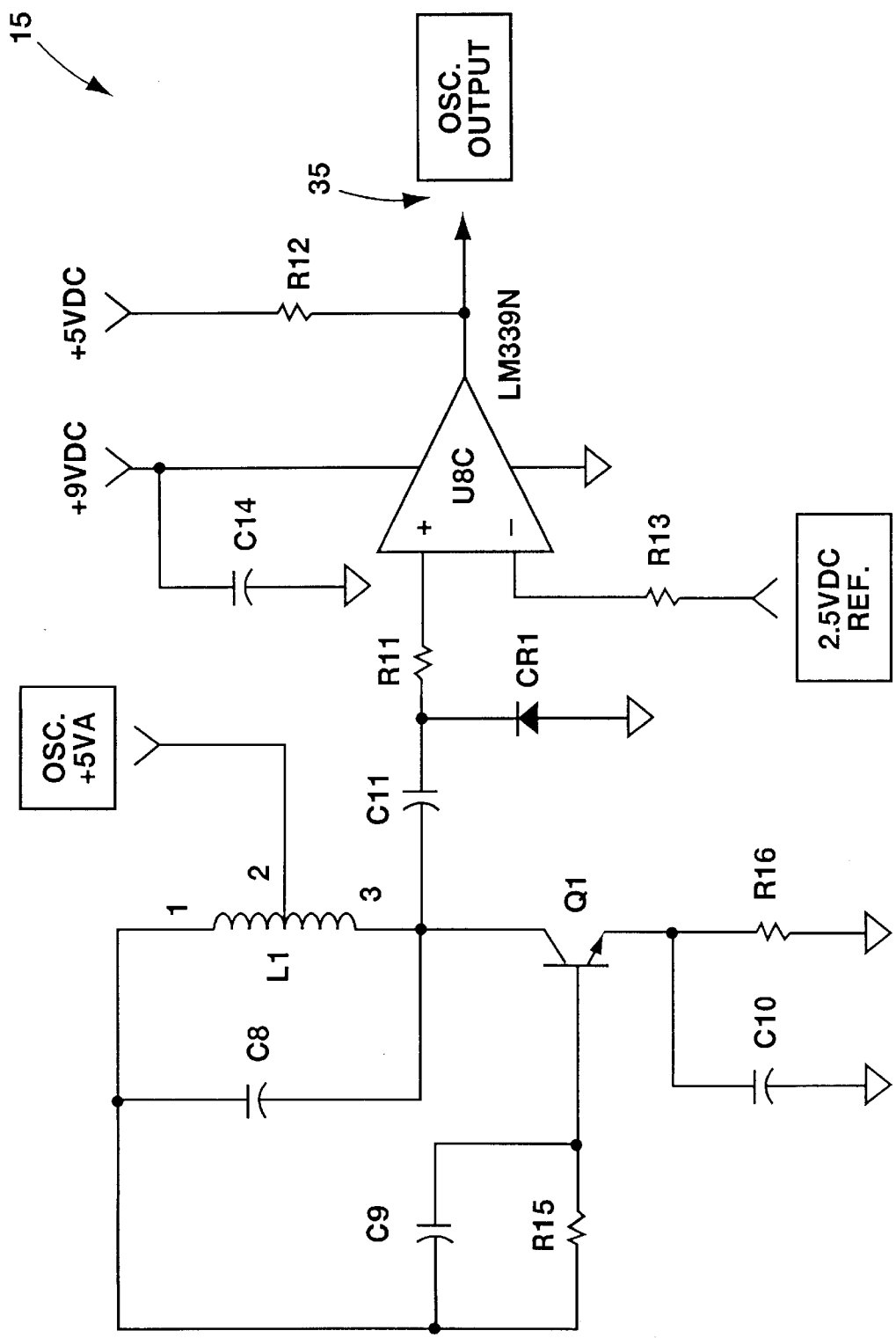
FIG. 2 is a detailed circuit diagram of the sample oscillator of FIG. 1.

Referring now to FIGS. 1 and 2, the sample oscillator is made up by coil 10 represented in the circuit diagram as inductor L1, transistor Q1, resistors R15 and R16 and capacitors C8, C9, C10 and C11 connected in a Hartley configuration. C8 and L1 determine the frequency of oscillation of the oscillator circuit.

Inductor L1 is of an open core form comprising a coil of wire wound on a hollow form 30 closed at the bottom, but open at the top to define a test chamber 31 into which the diamond to be tested is placed. The coil form opening 12 is circular, and of a diameter suitable for receiving a diamond of the size desired to test. A range of sizes can be tested with a form of a given opening. By way of example, an opening of from 7 to 9 millimeters can accommodate stones up to about 1.5 carats. The form opens upright so that the diamond stone to be tested may be dropped in from the top and removed by turning the tester case over. Alternatively, the stone can be temporarily attached to a strip of adhesive tape and lowered into the test chamber, or it can be inserted and removed with a pair of plastic tweezers.

The coil length is about 3/10ths of an inch with the test chamber 31 contained within the coil length. While it is preferred that the stone be fully placed within the test chamber for reproducibility of results, this is not critical. Nor is the portion of the stone within the coil and chamber; and, the stone may be placed either point end down or up.

The frequency of oscillation of the sample oscillator 15 changes when a synthetic diamond containing a small amount of ferrous material (typically iron and/or nickel) is placed in the test chamber 31 of the coil. The frequency does not significantly change when a natural diamond without any ferrous material is placed in the coil.

The output of the sample oscillator is isolated from the remainder of the detector circuits by integrated circuit U8C. This prevents the changing load at the OSC output from pulling the frequency of oscillation. The isolation circuit is made up of integrated circuit U8C, capacitor C14, resistors R11, R12 and R13. Diode CR1 prevents the input at integrated circuit U8C from going negative and being damaged.

The frequency of the sample oscillator is approximately 800 Khz. The diamond detector will function properly with an oscillator frequency of 100 Khz to 2 Mhz. The frequency can be changed by changing the value of C8 or the number of turns of the coil 10 comprising L1. The output of the sample oscillator is a continuous sine wave signal appearing at the oscillator output 35.

Reference Oscillator 16

Figure 3:
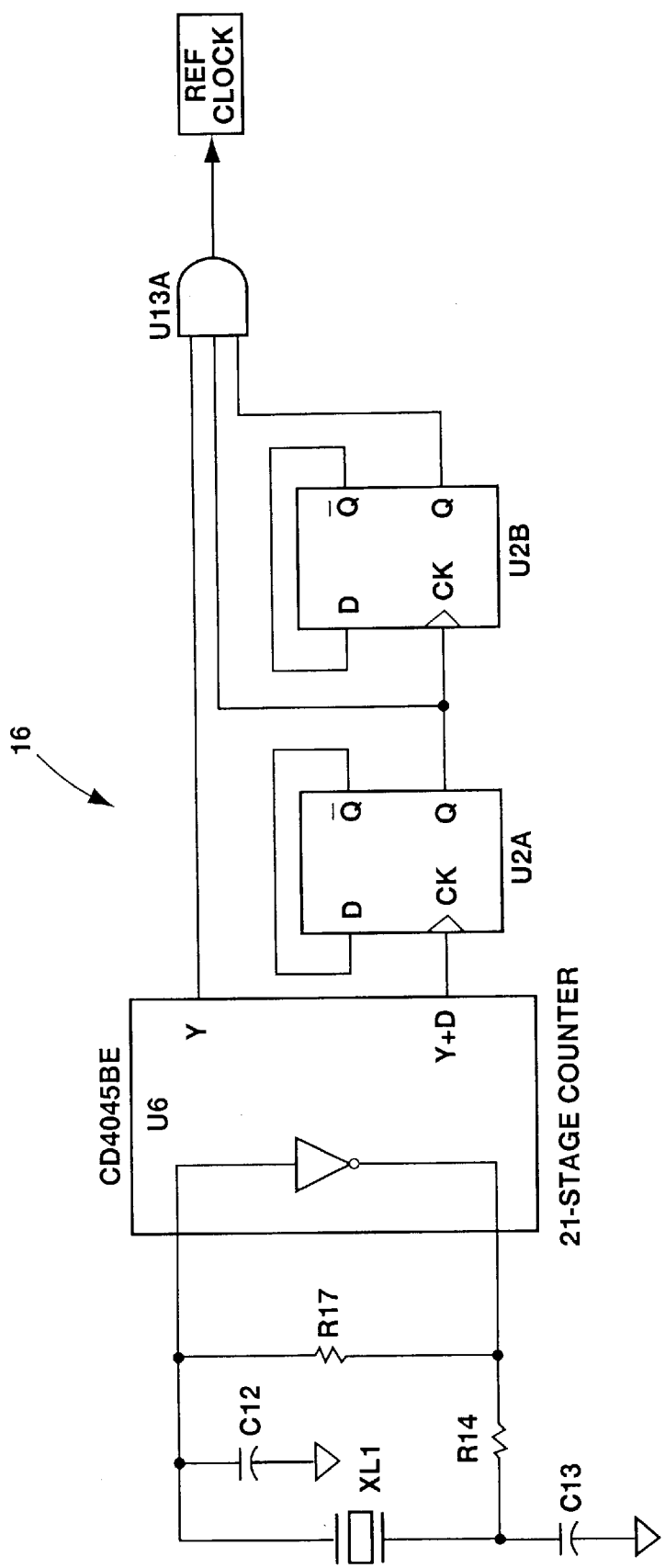
FIG. 3 is a detailed circuit diagram of the reference oscillator of FIG. 1.

Referring now to FIGS. 1 and 3, the reference oscillator 16 provides a stable, accurate and repeatable time interval for the calibrate and measurement cycles. The calibration and measurement cycles time interval must be equal to a high degree of accuracy for the diamond detector of the invention to work properly.

The reference oscillator 16 includes a crystal XL1, integrated circuit U6, resistors R14 and R17 and capacitors C12 and C13 which together form a stable crystal controlled oscillator. The frequency of oscillation is set by XL1.

The integrated circuit U6 also contains a 21 state counter which divides the crystal oscillator circuit by 2,097,152. Integrated circuits U2A and U2B form two divide by 2 circuits.

AND gate U13A gates the output of the three divider circuits to form the required stable, accurate and repeatable time intervals. See FIG. 4 for the timing diagram of the reference oscillator 16.

The satisfactory time interval from the reference oscillator (at REF CLOCK) is approximately 4 seconds. The diamond test circuit will function properly with time intervals from approximately ½ second to 8 seconds. The time interval can be changed by changing the crystal XL1.

Push to Test Switch Circuit 22

Figure 5:
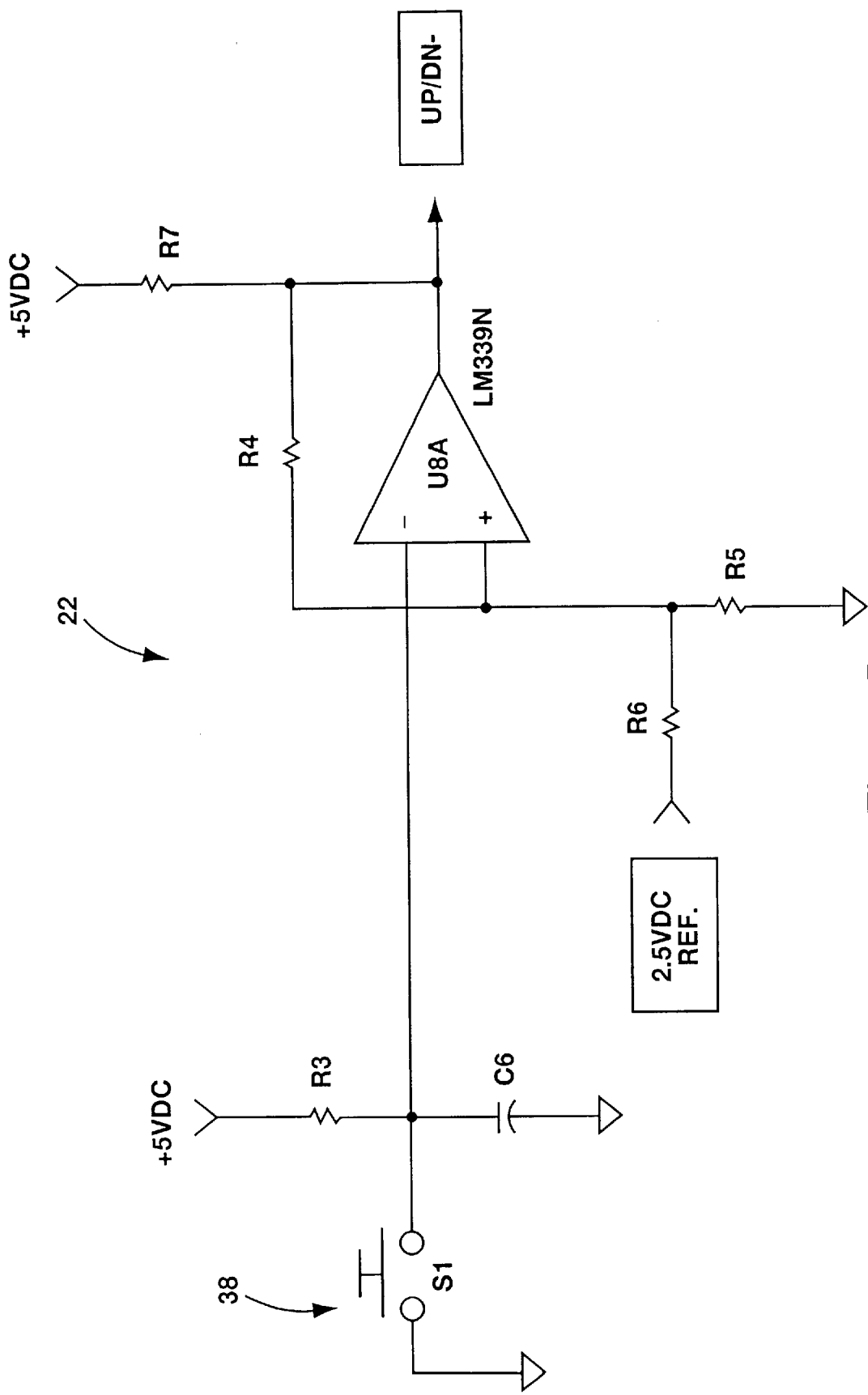
FIG. 5 is a detailed circuit diagram of the push to test circuit of FIG. 1.

Referring to FIGS. 1 and 5, the push to test circuit 22 includes a spring biased open switch S1 which controls the operation of the apparatus. When S1 is depressed, the output of integrated circuit U8A transitions to logic HI starting the up count or calibration cycle. When S1 is released the output of U8A transitions to logic LO starting the measurement cycle. Alternatively, S1 can be of a type that requires a second pressing to activate the second part of the cycle.

Resistor R3 :Ls used to provide a logic HI at the (−) input to integrated circuit U8A when S1 is not depressed. Capacitor C6 along with the hysteresis circuit around integrated circuit U8A work together to eliminate S1 switch bounce when S1 is depressed or released. Resistors R4, R5 and R6 form the hysteresis circuit around U8A. Resistor R7 at the output of U8A is used to pull the output of U8A to logic HI when S1 is depressed, as U8A has an open collector output.

Control Logic 20

Figure 6:
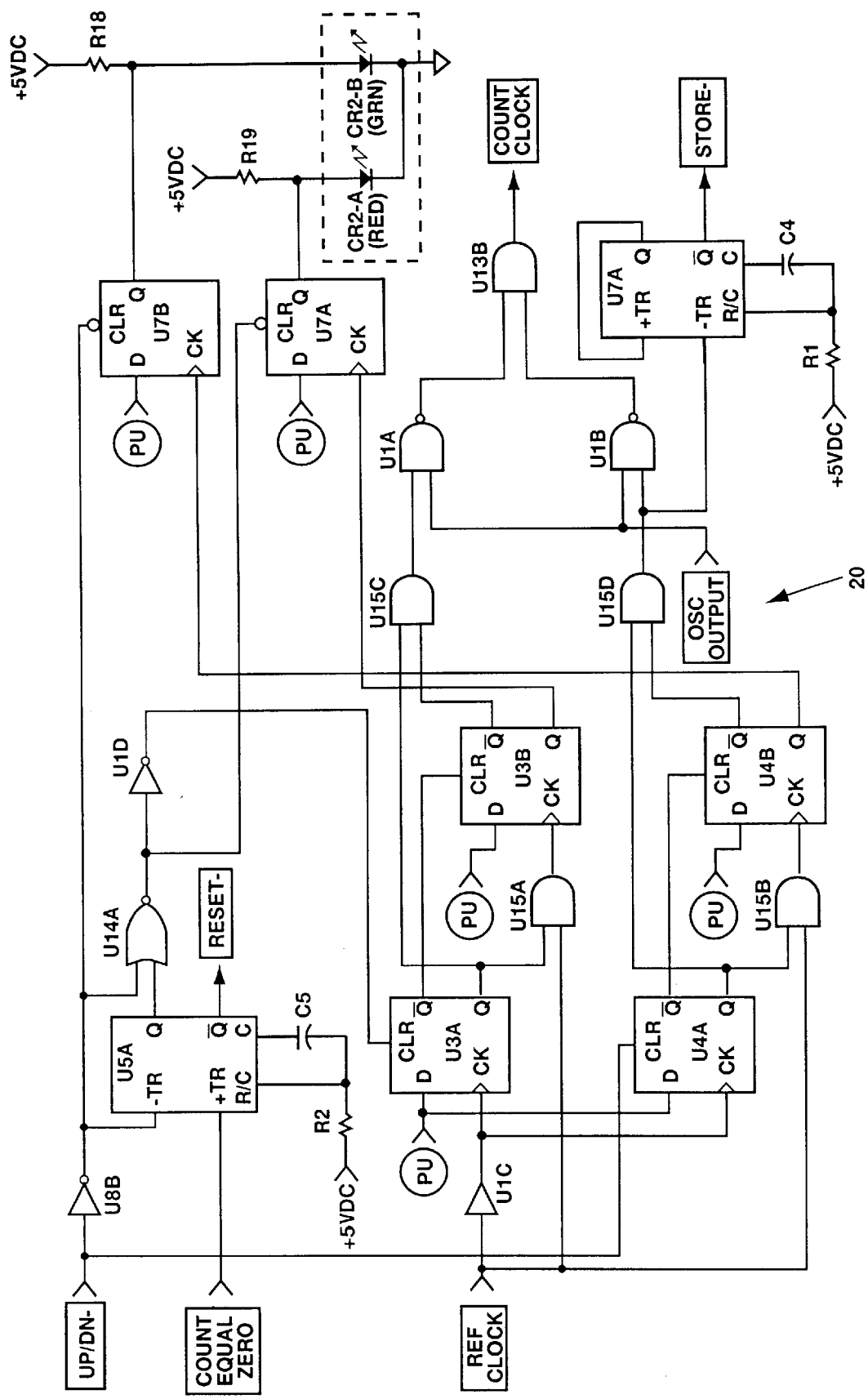
FIG. 6 is a detailed circuit diagram of the control logic circuits of FIG. 1.
Figure 7:
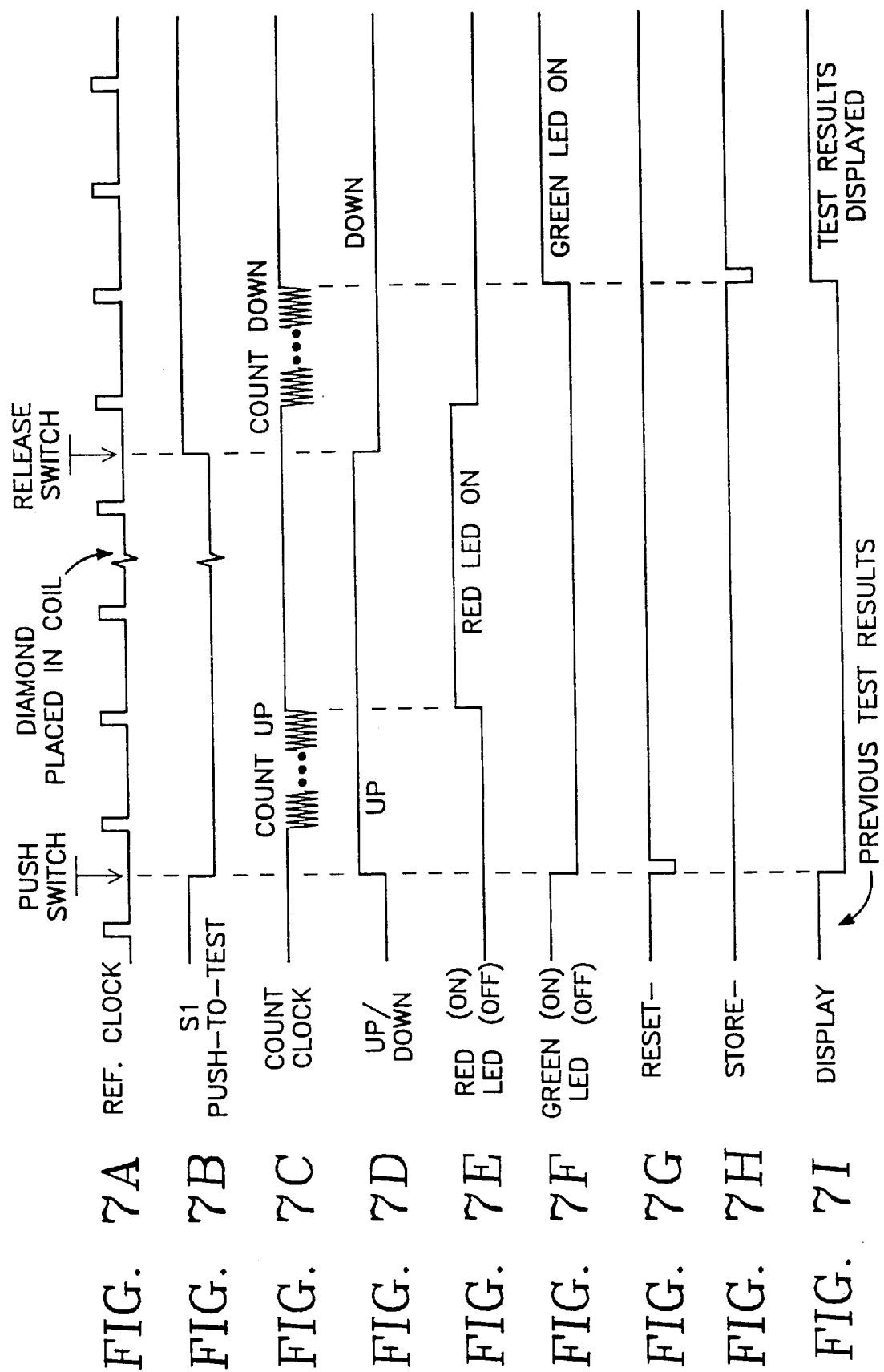
FIGS. 7A–7I is a set of timing signal graphs depicting the operation of the control logic and system of the detector of FIG. 1.
Figure 8:
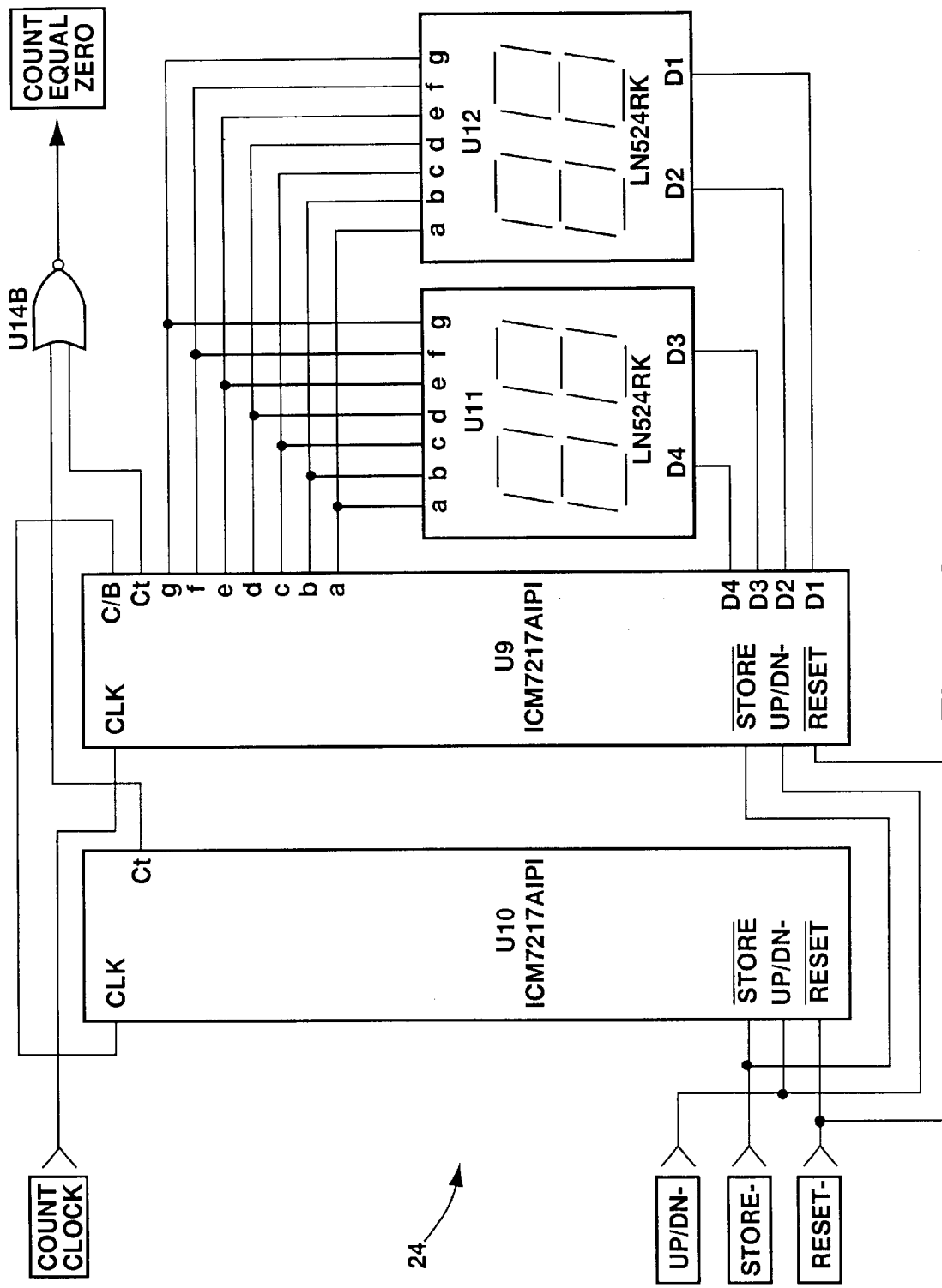
FIG. 8 is a detailed circuit diagram of the up/down counter and display circuits of FIG. 1.
Figure 9:
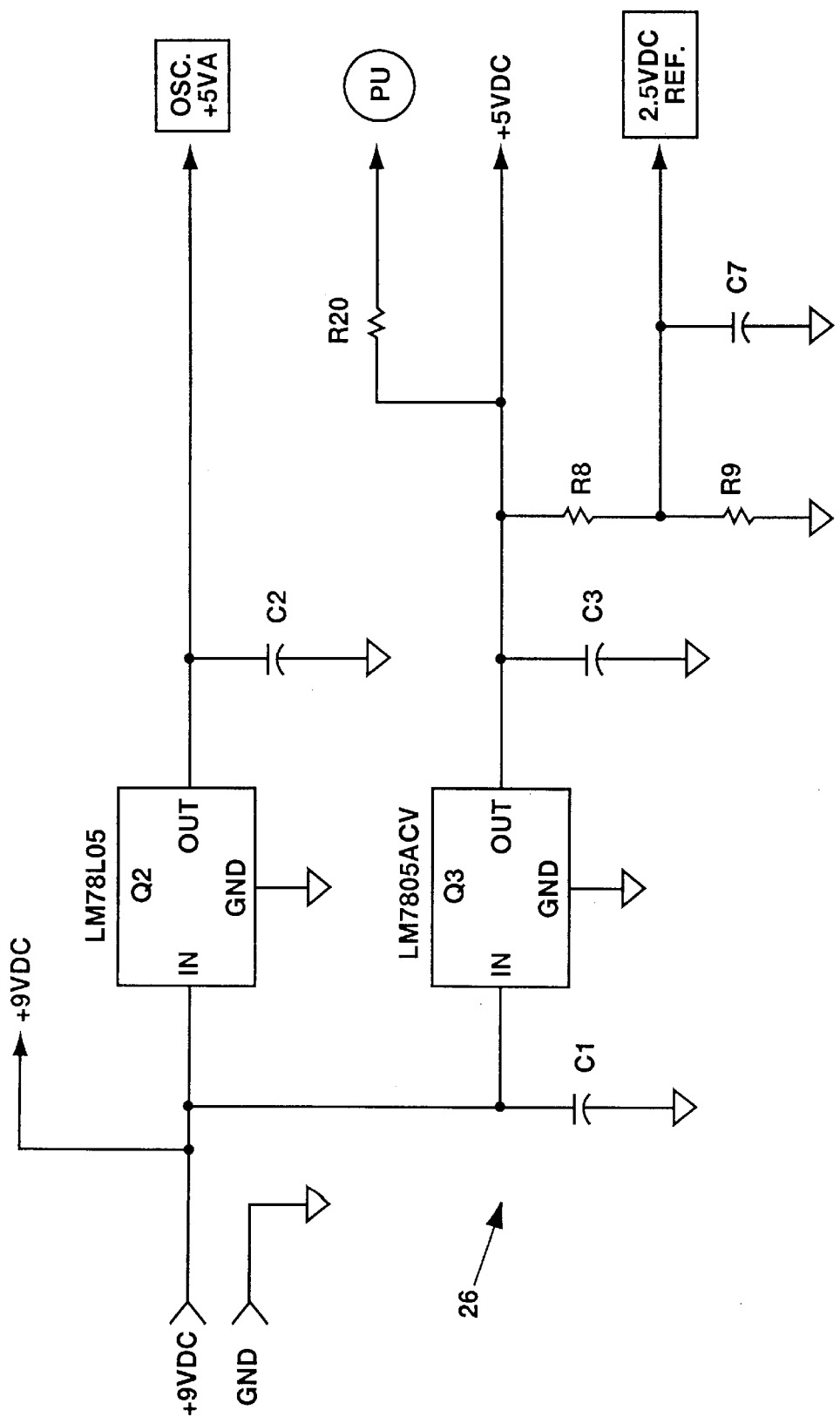
FIG. 9 is a detailed circuit diagram of the voltage regulator circuit of FIG. 1.

The control Logic is shown in FIGS. 1 and 6 and consists of three sections, as follows: a reset circuit, a count-up circuit, and a count-down circuit.

The reset circuit consists of integrated circuits U8B, U14A, U1D, resistor R2 and capacitor C5. R2 and C5 set the pulse width of the RESET- and send the clear pulse to integrated circuits U3A and U7A. Whenever the count of the up/down counter equals zero or the push to test switch S1 is depressed (UP/DN—transitions to logic HI), U5A outputs the RESET—and the clear pulse.

The count up circuit consist of integrated circuits U1C, U3A, U3B, U15A, U15C, U1A, U13B, U7A, LED CR2-A and resistor R19. Integrated circuits U3A and U7B are cleared when the push to test switch is depressed (UP/DN—transitions to Logic High). The green LED is turned off at this time. On the next high to low transition of the REF clock, the OSC output is gated to the Count Clock by integrated circuit U15C, U1A and U13B. Integrated circuit U3B is cleared at this time by integrated circuit U3A $\overline{Q}$ output starting the count up cycle. On the next low to high transition of the REF clock the OSC output is gated off at integrated circuit U13B output by integrated circuit U3B $\overline{Q}$, U15C and U1A. At this time integrated circuit U3B Q output clocks integrated circuit U7A turning on the red LED CR2-A indicating the up count or calibrate cycle is complete.

Count down circuit consist of integrated circuits U1C, U4A, U4B, U15B, U15D, U1B, U13B, U5B, U7B, LED CR2-B and resistor R18. Integrated circuits U4A and U7A are cleared when the push to test switch is released (UP/DN—transitions to logic L0). The red LED is turned off at this time. On the next HI to LO transition of the REF CLOCK the OSC OUTPUT is gated to the count clock by integrated circuit U15D, U1B and U13B. Integrated circuit U4B is cleared at this time by integrated circuit U4A $\overline{Q}$ output, starting the count down cycle. On the next LO to HI transition at the REF Clock the OSC output is gated off at integrated circuit U13B output by integrated circuit U4B $\overline{Q}$, U15D and U1B. At this time integrated circuit U4B Q output clocks integrated circuit U7B turning on the green LED CR2-B indicating the count down or measurement cycle is complete. Also at this time, integrated circuit U5B—TR input is clocked causing a STORE—pulse. Resistor R1 and capacitor C4 set the STORE—pulse width.

See FIGS. 7A–7I for control logic and system timing graphs.

Up/Down Counter Display 24

Integrated circuits (integrated circuit) U9 and U10 form an eight digit LED display driver with programmable up/down counter. This counter is controlled by the following four inputs and two sets of outputs "RESET-" This input when pulsed logic low will reset the counter to zero.

"STORE-" This input when pulsed logic low will store the existing value of the counter and cause it to be displayed on the four digit display U11 and U12.

"UP/DN-" This input when logic HI causes the counter to count up one count for each "COUNT CLOCK" cycle. When logic low the counter will count down.

"COUNT CLOCK" Each cycle of the count clock causes the count to count up or down one count depending on the state of "UP/DN-".

"COUNT EQUAL ZERO" This output goes logic HI when the count of both integrated circuit U9 and U10 equal zero.

Display drive a,b,c,d,e,f,g,D1,D2,D3 and D4 drive LED display integrated circuit U11 and U12.

Voltage Regulator 26

The voltage regulator has two (2) +5vDC regulator circuits. One for the sample oscillator circuit and one for the remainder of the diamond test circuit. The separate voltage regulator for the sample oscillator improves the sample oscillators stability.

Voltage regulator integrated circuit Q2 and capacitor C2 form the sample oscillator +5vAC supply. Capacitor C2 stores energy and reduces ripple at the output of Q2.

Voltage regulator integrated circuit Q3 and capacitors C1 and C2 form the +5vDC supply for the remainder of the detectors circuits. Capacitor C1 and C2 store energy and reduce supply ripple.

Resistor R20 output provides a logic HI pull up (PU) for the logic inputs that need to be a logic HI at all times. Resistor R8 and R9 form a resistive divider to produce a 2.5vDC reference voltage. Capacitor C7 provides decoupling for the 2.5vDC reference. A +9vDC level is provided to the diamond detector by a standard UL approved regulated wall mount power supply.

System Operation

In summary, the diamond test has four operator interface indicators and controls. They are the push-to-test switch, 4 digit LED (should this not be liquid crystal) display, red and green LED indicators and the sample coil.

The sequence of operation of the diamond detector is as follows (after plugging in the +9vDC wall mount power supply and allowing the detector approximately 5 minutes to warm-up):

The push-to-test switch 22 is pressed FIG. 7B) and held down. The green LED CR2-A will go out (FIG. 7F). After approximately 6 seconds the red LED CR2-B will illuminate (FIG. 7E) indicating the completion of the calibration cycle in which the count clock counts up the number of sample oscillator cycles (FIG. 7C) during the calibration interval (FIG. 7A).

2) The diamond to be tested is placed in the sample coil and the push-to-test switch is released FIG. 7B). The red LED will go out at this time FIG. 7E).

3) During the next available interval (FIG. 7A) the count clock recounts as a down-count the sample oscillator cycles (FIG. 7C). After approximately 6 seconds the green LED will illuminate (FIG. 7F) indicating completion of the measurement cycle and test. The STORE signal is given to the display circuits (FIG. 7H) and the results displayed (FIG. 7I). At this time the results of the test will be displayed on the four digit display.

It is found that stable oscillators will result in count differences between natural and synthetic stones of above about 25 counts for signals having total count values of about 2 million. This leads to the requirement that the counting circuits be stable over the testing process time to less than that value, preferably to about one (1) part per million for 5–10 seconds. Stability is easily checked, by the way, by performing the entire sequence without a sample stone in place. This should result in a count of less than 3 cycles.

As an example of the criteria for a synthetic stone identification in accordance with the present invention, for a sample oscillator frequency of 800 Khz, and a sampling interval of 4 seconds, it is expected that no natural stone will result in a count difference greater than 25 cycles. Any value greater than 25 cycles should be considered to be likely to have resulted from testing a synthetic diamond.

While the invention has been disclosed in a form for ready implementation in discrete logic circuits, it is to be understood that the reference oscillator, control logic circuits and counting circuits could readily be implemented on a computer chip with appropriate programming.

Figure 10:
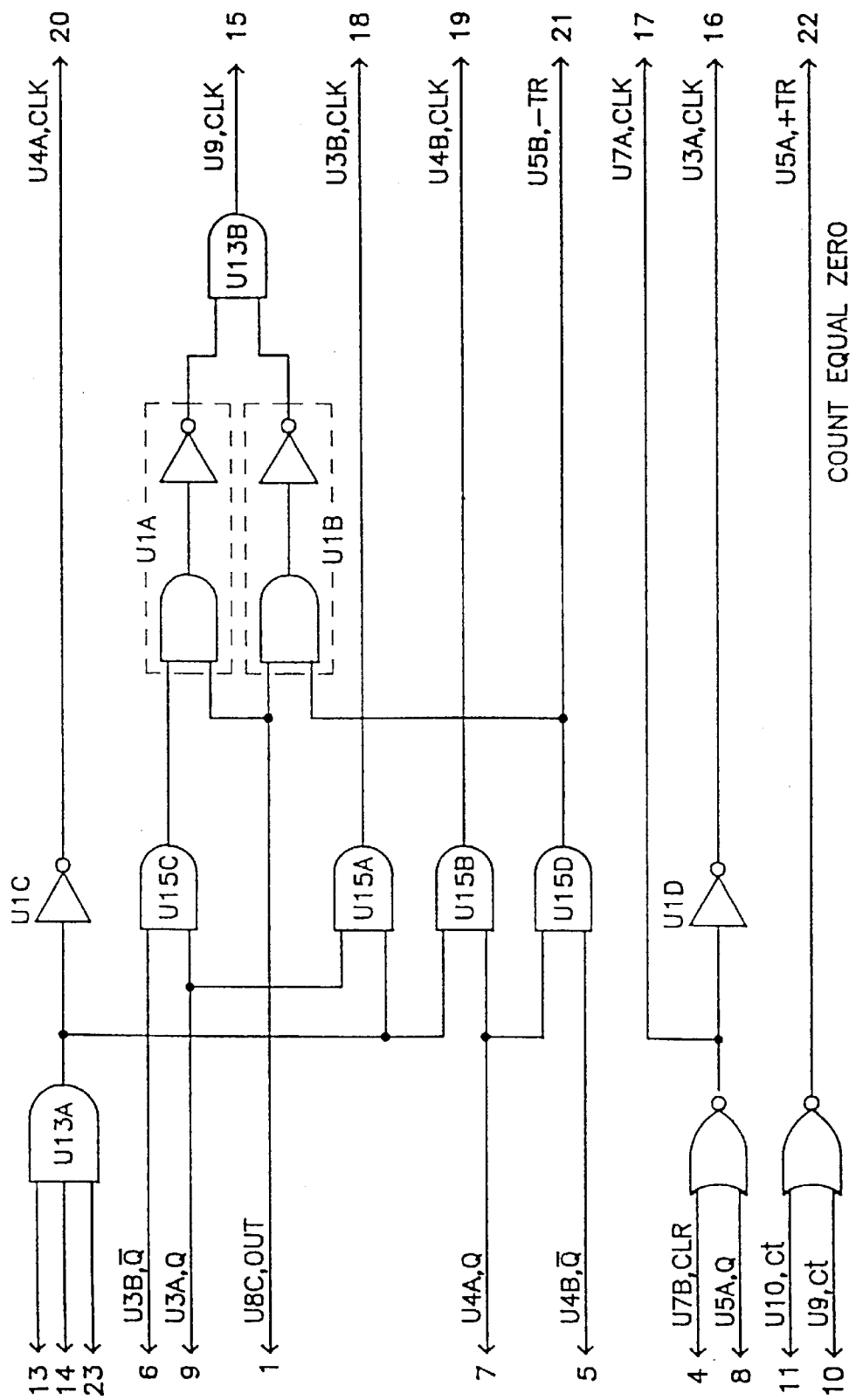
FIG. 10 is a logic diagram for programming a programmable logic device for use in an alternate embodiment of the invention.

By way of an example, and referring to FIG. 10, there is shown a logic diagram representing the logic circuit program for a 20V8 PLD (programmable logic device) chip. Such a PLD chip is provided with an internal logic gate block for realizing a logic circuit specified by the user in the form of a circuit configuration data written into a memory circuit. The form of circuit configuration is the logic circuit itself such as is shown in FIG. 10. After receiving the logic circuit configuration, the PLD chip performs in accordance with that logic. When so programmed according to the logic of FIG. 10, the 20V8 PLD chip can directly replace the entire circuit of FIG. 6. The 20V8 PLD pin assignments are given as arrowed references 1–23 in FIG. 10. The equivalent connections for substituting the chip into the previously described circuit of FIGS. 1–9 are given immediately over the respective leads, as U3A,Q . . . U10,Ct. It is not necessary to set forth the programming in detail as the logic configuration shown is used directly for programming the PLD chip. Such logic chips are available from Advanced Micro Devices of Sunnyvale, Calif. and from Monolithic Memories of Sunnyvale, Calif., among others. By using a programmable logic device the size and cost of the circuits is reduced.

Figure 12:
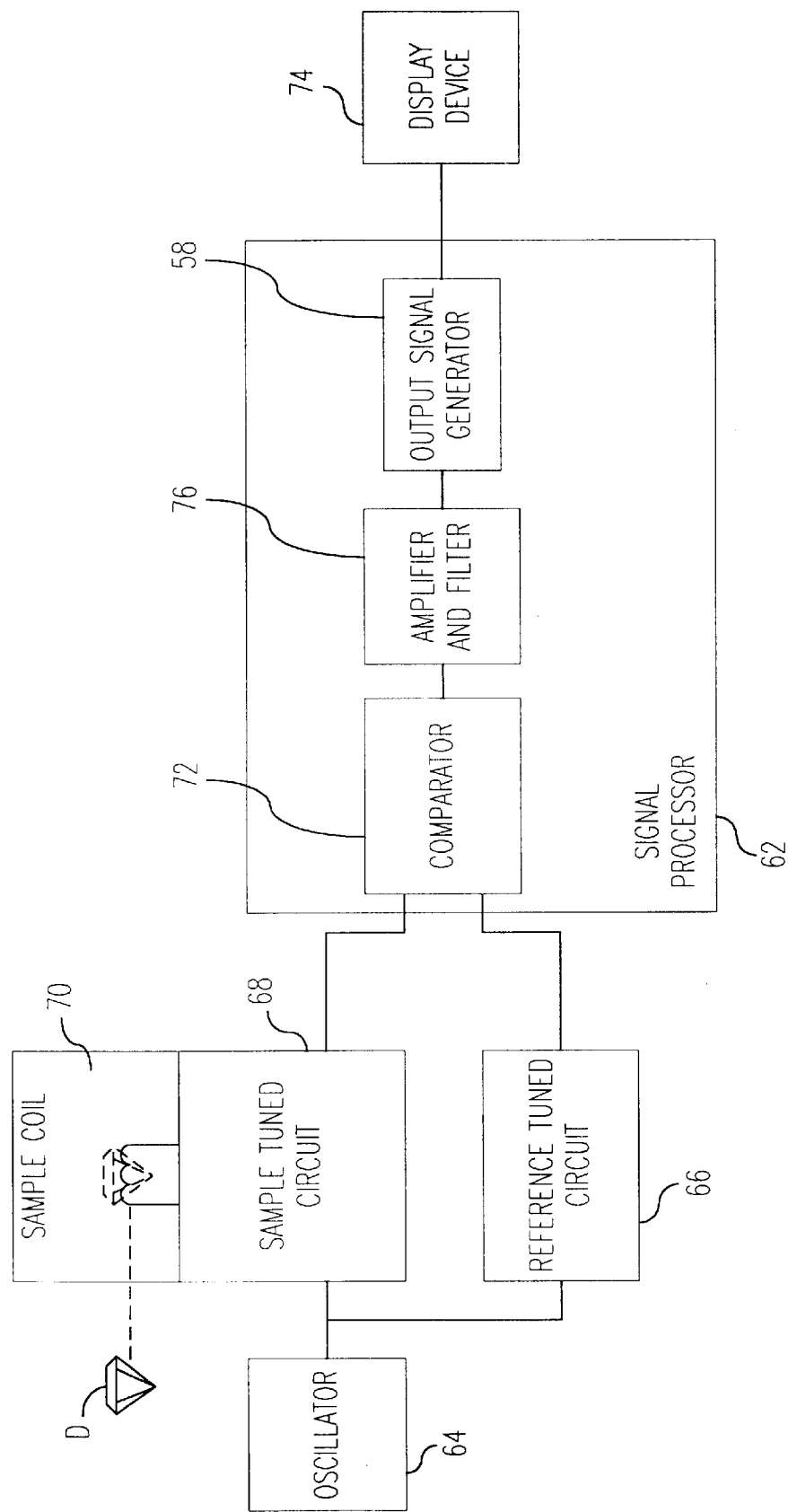
FIG. 12 is a block diagram of a device constructed according to a second embodiment of the present invention that screens a diamond sample using a tuned circuit.

Referring now to FIG. 12, the second embodiment of the present invention screens a diamond sample by detecting a change in the output amplitude of a tuned circuit that results from placing the sample in a coil of the tuned circuit. An oscillator 64 (FIG. 12, left) and a sample tuned circuit 68 substantially provide the functionality of the magnetic field alteration detector 54 of FIG. 11. The remaining components of FIG. 12 substantially provide the functionality of the signal processor 62 and the output device 60 of FIG. 11.

The fixed frequency oscillator 64 generates a signal that drives two tuned circuits: a reference tuned circuit 66 and the sample tuned circuit 68. The two tuned circuits are identical except that the sample tuned circuit 68 has a sample coil 70 adapted to receive a diamond sample D. The outputs of the two tuned circuits drive a comparator 72. When a diamond sample D is not present in the sample coil 70, the output signals from the two tuned circuits are virtually identical. As a result, the comparator 72 does not generate an output signal. When a diamond sample D is placed in the coil, the Q of the sample coil 70 changes. This, in turn, changes the amplitude of the output signal of the sample tuned circuit. The comparator 72 senses the difference in the outputs of the two tuned circuits and generates an output signal. The output of the comparator 72 is amplified, filtered and processed to generate a signal that drives a display device 74. The display device 74 provides a visual indication of whether the diamond sample D is synthetic or natural.

Figure 13A:
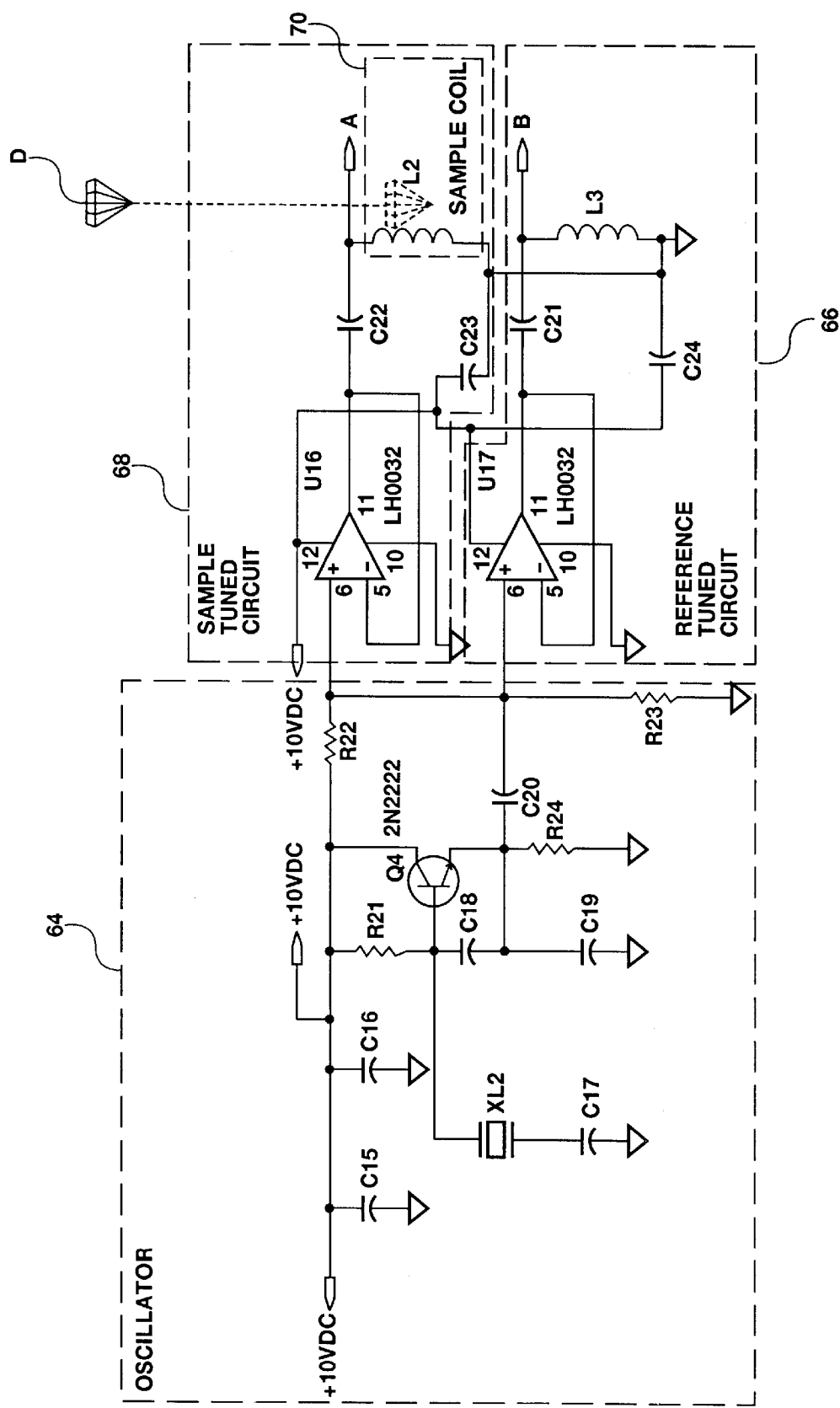
FIGS. 13A, 13B, 13C and 13D are detailed circuit diagrams of the device of FIG. 12.

A detailed circuit diagram of the embodiment of FIG. 12 is depicted in FIGS. 13A, 13B, 13C and 13D. Referring to FIG. 13A, a crystal controlled oscillator circuit 64 (left) drives a reference tuned circuit 66 and a sample tuned circuit 68. The oscillator circuit 64 is comprised of crystal oscillator XL2, transistor Q4, capacitors C17, C18 and C19, and resistors R21 and R24. The output signal of transistor Q4 feeds capacitor C6 and a voltage divider comprised of resistors R22 and R23. This signal drives the reference tuned circuit 66 and the sample tuned circuit 68.

As shown in FIG. 13A, the oscillator circuit 64 can be constructed from relatively inexpensive electronic components. For example, oscillator XL2 is a fixed-frequency crystal oscillator. Typically, the oscillator has an operating frequency between 2 to 8 megahertz. Transistor Q4 is a low-cost general purpose transistor. The construction and operation of oscillator circuits such as the one depicted in FIG. 13A are well known in the electronics art. Accordingly, the oscillator circuit will not be discussed further.

The reference tuned circuit 66 generates a reference signal that is compared by the comparator 72 (FIG. 13B) to a signal from the sample tuned circuit 68. The operation and construction of tuned circuits are well known in the electronics art. Accordingly the operation of the tuned circuits will be discussed in general terms.

The frequency response of a tuned circuit describes the relationship between the frequency of the signal driving the tuned circuit and the output amplitude of the tuned circuit. Graphically, the frequency response resembles a "bell curve" where the output is maximum at the resonant frequency of the tuned circuit and is progressively lower at frequencies above and below the resonant frequency. The steepness of the bell curve near the resonant frequency is related to a characteristic of the tuned circuit known as the "Q" of the circuit. A tuned circuit with a high Q has a relatively steep curve near the resonant frequency. In other words, relatively small changes in the input frequency produce relatively large changes in the output amplitude of the tuned circuit. Similarly, the phase shift between the input and output signals of a high Q tuned circuit is relatively sensitive to a change in the input frequency when the input frequency is near resonance. In sum, a high Q tuned circuit is relatively sensitive to changes in the frequency of the input signal particularly when the frequency of the input signal is near the resonant frequency of the tuned circuit.

In a similar manner, a high Q tuned circuit is relatively sensitive to changes in the inductive components of the tuned circuit when the input signal frequency is near resonance. A change in the inductance of a tuned circuit changes the Q and the resonant frequency of the tuned circuit. This causes the output amplitude and phase shift of the tuned circuit to change. Moreover, as discussed above, when the input frequency is near resonance, the tuned circuit is particularly sensitive to changes in the resonant frequency relative to the input frequency. As a result, when the input signal frequency is held constant at the resonant frequency, a relatively small change in the parameters (e.g., inductance or Q) of the tuned circuit produces a relatively large change in the output signal amplitude and phase shift of the tuned circuit.

The reference tuned circuit 66 of FIG. 13A includes operational amplifier U17, capacitor C21 and inductor L3. The operational amplifier U17 along with the operational amplifier U16 in the sample tuned circuit 68 provide isolation between the tuned circuits and the signal from the oscillator circuit 64. This isolation prevents a change in one of the tuned circuits from affecting the signal that drives the tuned circuits. The capacitor C21 and inductor L3 in the reference tuned circuit 66 are the capacitive and inductive elements for the tuned circuit, respectively. Thus, the values for capacitor C21 and inductor L3 are selected to make the resonant frequency of the tuned circuit approximately equal to the frequency of the oscillator circuit 64 and to give the tuned circuit a relatively high Q. For example, typical component values when the oscillator frequency is approximately 2.4 megahertz are 16 microhenries for inductor L3 and 270 picofarads for capacitor C21.

The sample tuned circuit 68 is identical to the reference tuned circuit 66 except that the sample coil 70 (i.e., inductor L2) is adapted to receive a diamond sample D within its core. When a diamond sample D is not in sample coil 70 (as represented by the diamond sample D with solid lines), the outputs of the two tuned circuits are virtually identical. However, when a synthetic diamond is placed in sample coil 70 (as represented by the diamond sample D with dashed lines), the inductance of the tuned circuit changes (typically in the order of a few hundred nanohenries, depending on the amount of iron in the sample). This, in turn, changes the output of the sample tuned circuit 68. The outputs of the sample tuned circuit 68 and the reference tuned circuit 66 feed reference point A and reference point B, respectively.

Figure 13B:
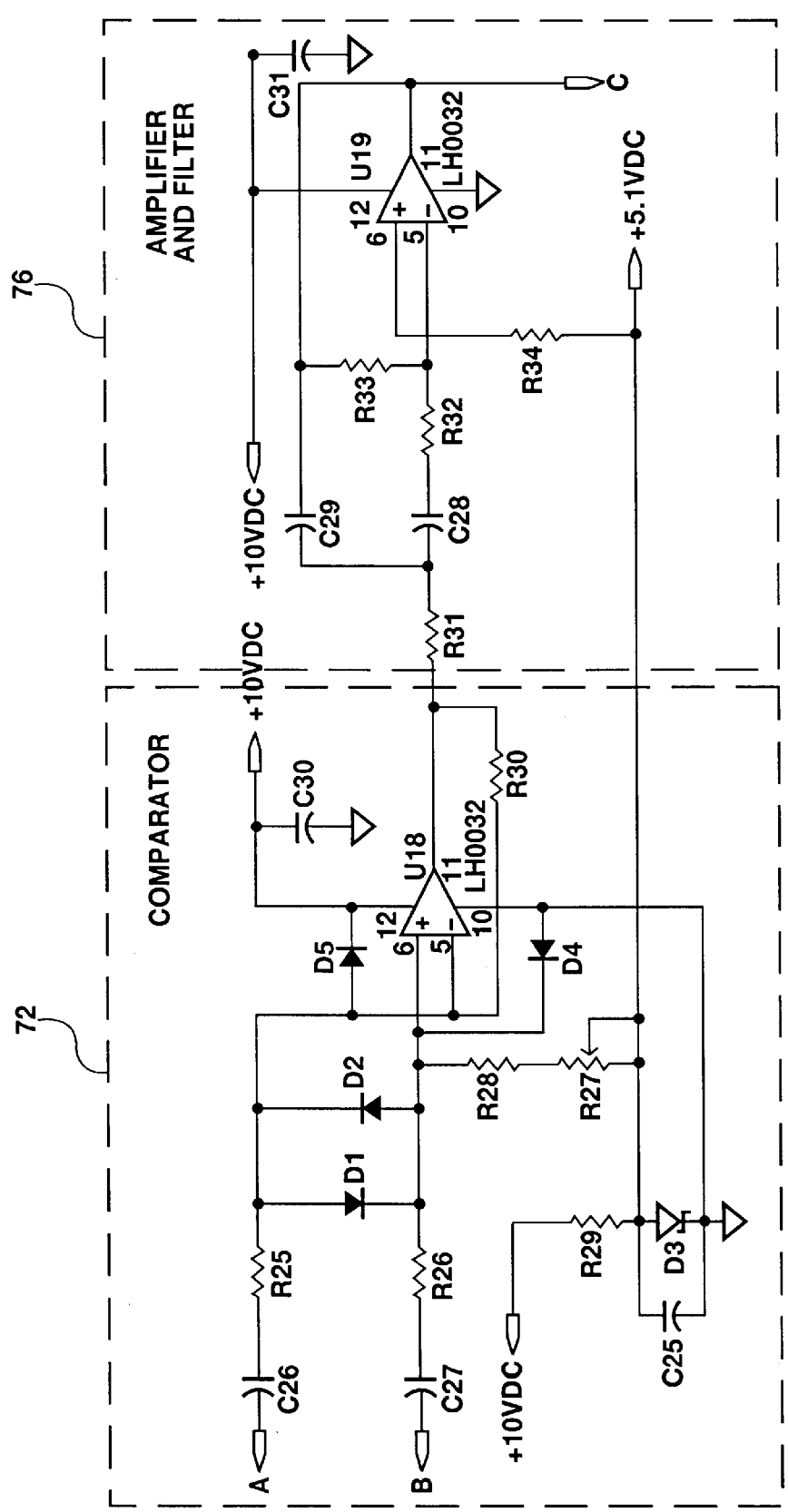

Referring to FIG. 13B, a comparator 72 (left) compares the outputs of the two tuned circuits. The comparator 72 includes an operational amplifier configured as a differential amplifier U18. The output signal from the sample tuned circuit 68 (FIG. 13A) flows from reference point A through capacitor C26 and resistor R25 to one input of the differential amplifier U18. The output signal from the reference tuned circuit 66 (FIG. 13A) flows from reference point B through capacitor C27 and resistor R26 to the other input of the differential amplifier U18.

Ideally, when the input signals of the differential amplifier are equal, the differential amplifier U18 should not generate an output signal. However, due to factors such as the variations that occur during the operational amplifier manufacturing process, differential amplifier U18 typically generates a small output signal when a diamond sample D is not in the sample coil 70. To compensate for this signal, resistor R8 and potentiometer R7 provide an adjustment in the differential gain of the differential amplifier U18. Proper adjustment of potentiometer R7 can result in a null of 45 to 50 DB below the nominal signal output of the differential amplifier U18. The operation and construction of differential amplifier circuits are well known in the electronics art. Accordingly, these aspects of the circuit will not be discussed in detail.

When a diamond sample D containing ferrous material is placed in the sample coil 70 (FIG. 13A), the differential amplifier U18 produces an output signal due to the small difference between the amplitude and phase shift of the signals at its inputs. Typically, the amplitude of the signal at the output of the differential amplifier is in the range of a few hundred microvolts. Depending on the ferrous content of the synthetic diamond, however, signals in the millivolt range are possible.

The output of the differential amplifier U18 is amplified and filtered by the amplifier and filter circuit 76. The operational amplifier U19, resistors R31 and R32, and capacitors C28 and C29 comprise an active bandpass filter that filters out noise at frequencies above and below the frequency of the signal generated by the oscillator circuit 64 (FIG. 13A). In addition, U19 in conjunction with resistors R33 and R34 amplifies the signal generated by the differential amplifier U18. Typically, the amplifier provides a gain of approximately 1000:1. The amplified signal flows to reference point C (right).

Figure 13C:
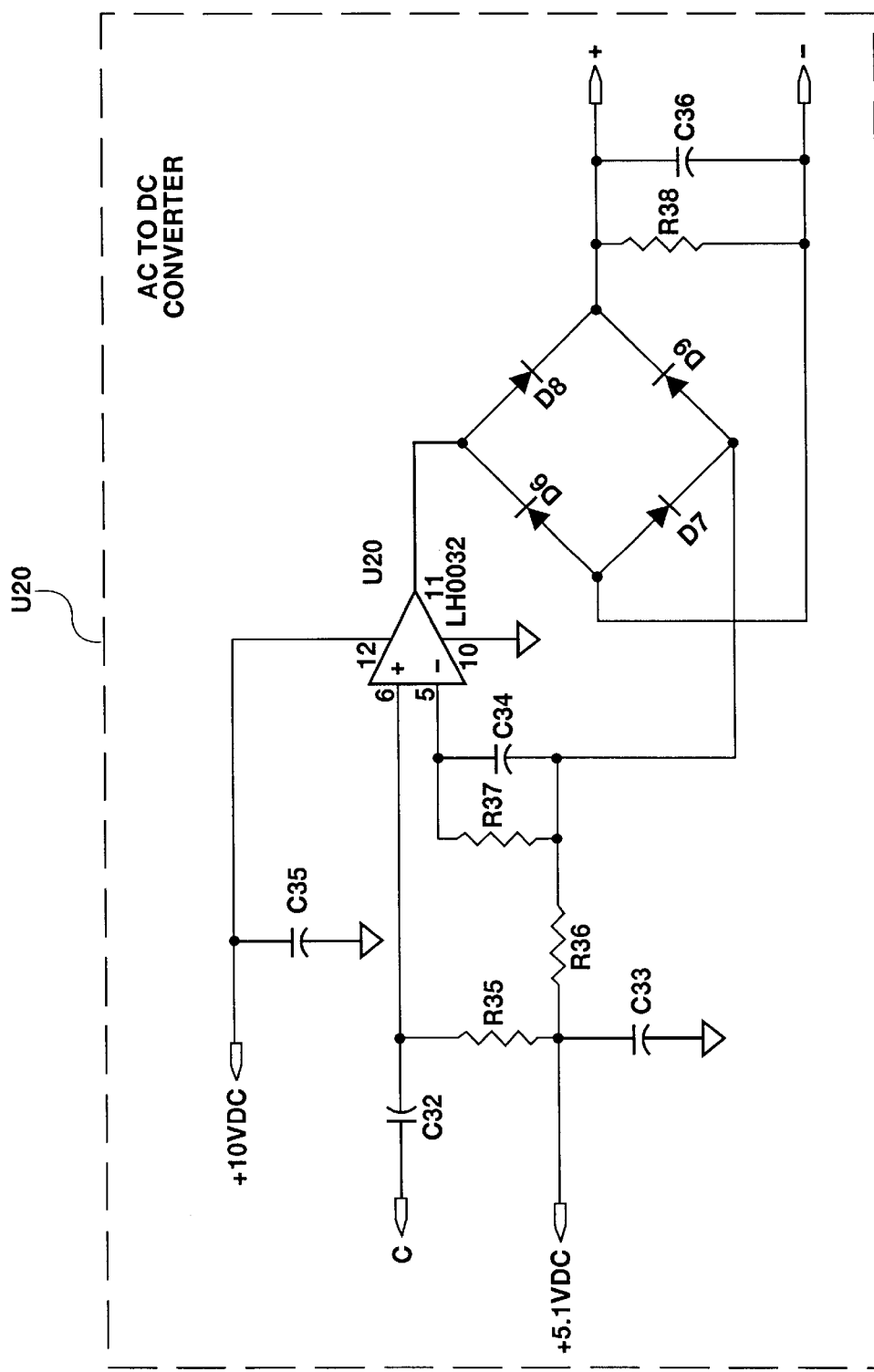

Referring now to FIG. 13C, an AC-to-DC converter 78 converts the alternating current ("AC") signal at reference point C (left) to a direct current ("DC") signal. Capacitor C32 and operational amplifier U20 provide coupling and DC isolation for the circuit. Diodes D6, D7, D8 and D9 form a bridge rectifier in the feedback path of the operational amplifier U20. This configuration eliminates the error caused by the diodes' voltage drop variation. Resistor R37 converts the current output of the diode bridge to a voltage. Capacitors C34 and C36 filter the signal output by the AC-to-DC converter.

Figure 13D:
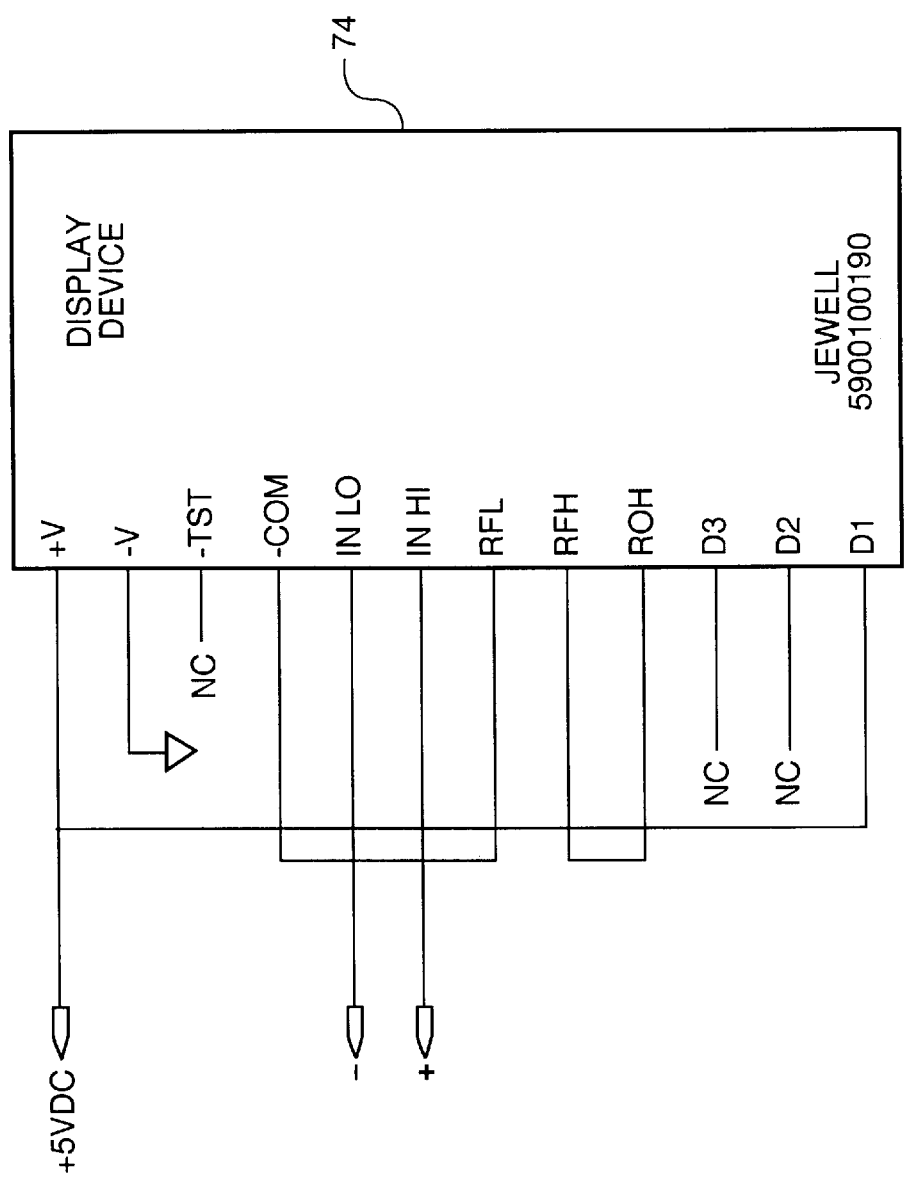

The output of the AC-to-DC converter is fed through reference points "+" and "−" (right) to a display device 74 (FIG. 13D). The display device 74 is a single chip digital volt meter with a digital readout. The digital readout displays a number indicative of the probability that the diamond sample D (FIG. 13A) placed in the sample coil 70 is a synthetic diamond.

This embodiment typically provides a more sensitive screening device than the first embodiment. First, the fixed frequency crystal controlled oscillator is not subject to as much frequency drift as the oscillator of the first embodiment. Second, the tuned circuit is more sensitive to changes in the effective coil parameters than many other comparable circuits. Third, the differential amplifier provides a very deep null and, as a result, can detect very small differences in the output signals of the tuned circuits. Moreover, the second embodiment can be constructed using relatively inexpensive components. Thus, this embodiment provides a relatively sensitive and inexpensive apparatus for screening diamond samples.

Figure 14:
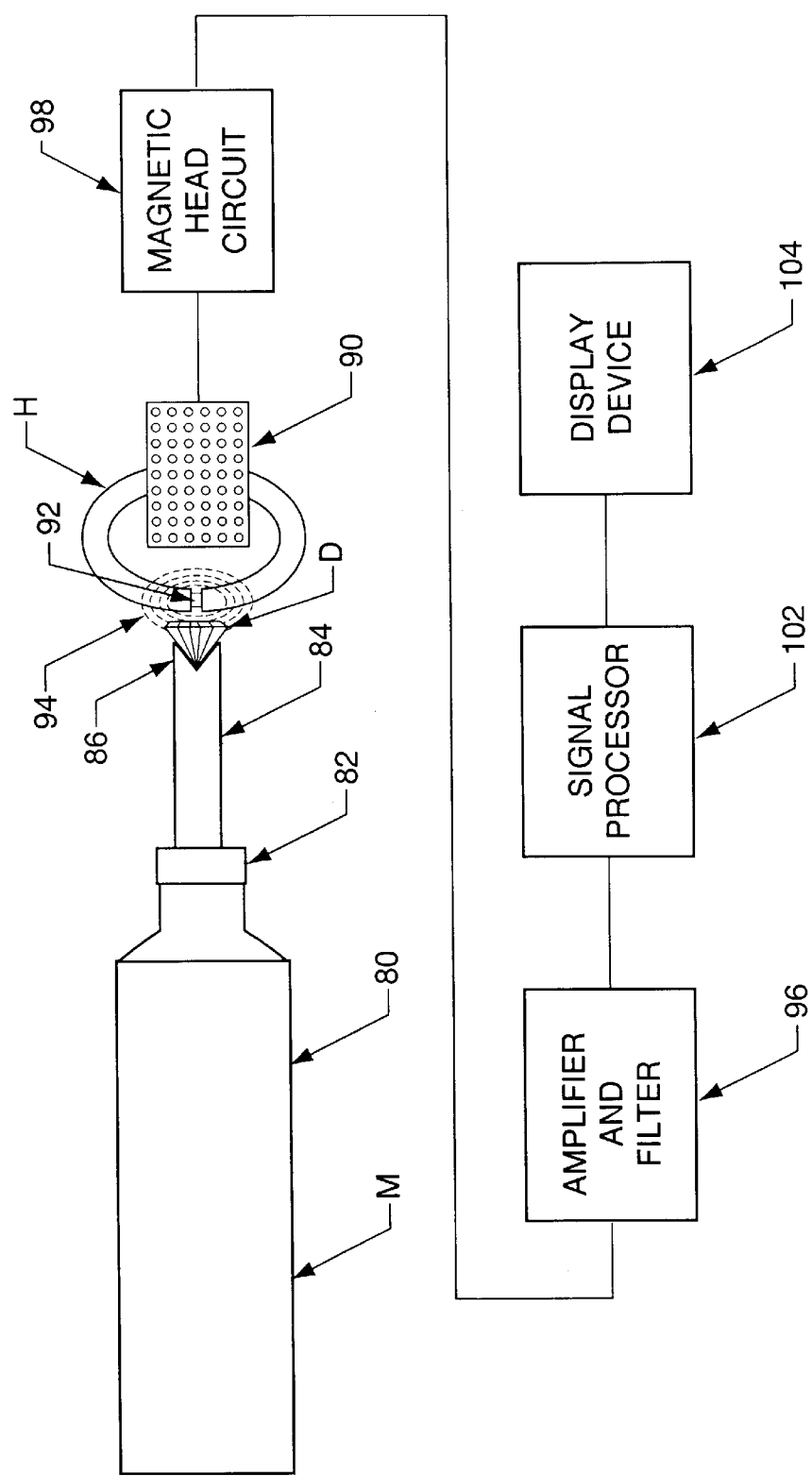
FIG. 14 is a hybrid pictorial diagram and block diagram of a device constructed according to a third embodiment of the present invention that screens a diamond sample by moving the sample in a magnetic field.

Referring to FIG. 14, the third embodiment of the present invention screens a diamond sample by detecting a signal generated when the sample is rotated in a magnetic field. A motor assembly M, an air-gap magnetic head H and a magnetic head circuit 98 substantially provide the functionality of the magnetic field alteration detector 54 of FIG. 11. The remaining components of FIG. 14 substantially provide the functionality of the signal processor 62 and the output device 60 of FIG. 11.

In this embodiment, the present invention is based, in part, on the realization that ferrous inclusions in a synthetic diamond are not evenly distributed within the diamond. As a result, the inclusions disturb a magnetic field when they are rotated within the field. Accordingly, the diamond sample D is positioned within a magnetic field generated by the magnetic head H, then rotated by the motor assembly M. When the diamond sample D is a synthetic diamond, the ferrous material in the diamond sample D disturbs the magnetic field thereby inducing a small alternating current signal in a coil 90 of the magnetic head H. This signal is amplified, filtered and processed to display the probability that the diamond sample D is synthetic.

The motor assembly M is comprised of a motor 80, a chuck 82 and a shaft 84 that is adapted to receive a diamond sample D. In general, to prevent the detected signal from being corrupted by ambient noise (e.g., 60 Hertz AC), the diamond must be rotated at a relatively high speed to produce a signal with a frequency that is higher than the ambient noise frequencies. Typically, the motor 80 operates at 25,000 to 30,000 revolutions per minute. The chuck 82 fastens the motor shaft 84 to the motor 80. The motor shaft 84 is a dielectric shaft, typically made of plastic, wood or other non-ferrous material. The diamond sample D is connected to the motor shaft 84 using an adhesive 86 such as DOP wax or glue. Alternatively, any other suitable connecting method can be used. Typically, a small portable motor such as one sold by Dremel Corporation (commonly known as a "Dremel Tool") can be used for motor 80.

The magnetic head H generates the magnetic field and detects a disturbance in the magnetic field caused by a rotating synthetic diamond. The magnetic field is generated by a DC current running through the coil 90 of the magnetic head H. This magnetic field is concentrated at an air-gap 92. In FIG. 14, the magnetic field is represented by magnetic field lines 94.

The magnetic head H and the motor assembly M are mounted so the diamond sample D attached to the motor shaft 84 can be positioned near the air-gap 92 of the magnetic head H. Typically, the distance between the diamond sample D under test and the magnetic head is in the range of a few thousandths of an inch.

The magnetic head H can be constructed from relatively common components. For example, a read/write head from a relatively inexpensive tape recorder can generate acceptable signals. Tests have also indicated that a head with a relatively large air-gap may provide better results than a comparable head with a very small air-gap.

A diamond sample D is tested by rotating the sample in the magnetic field generated by the magnetic head H. When the sample is a synthetic diamond, the deposits of ferrous material in the diamond disturb the magnetic field generated by the magnetic head H. This disturbance in the magnetic field, in turn, generates a signal in the coil 90 of the magnetic head H. Typically, the amplitude of the detected signal is in the order of one to ten microvolts. An amplifier and filter circuit 96 amplifies this signal to a suitable level for processing and filters the signal to remove noise.

Figure 15:
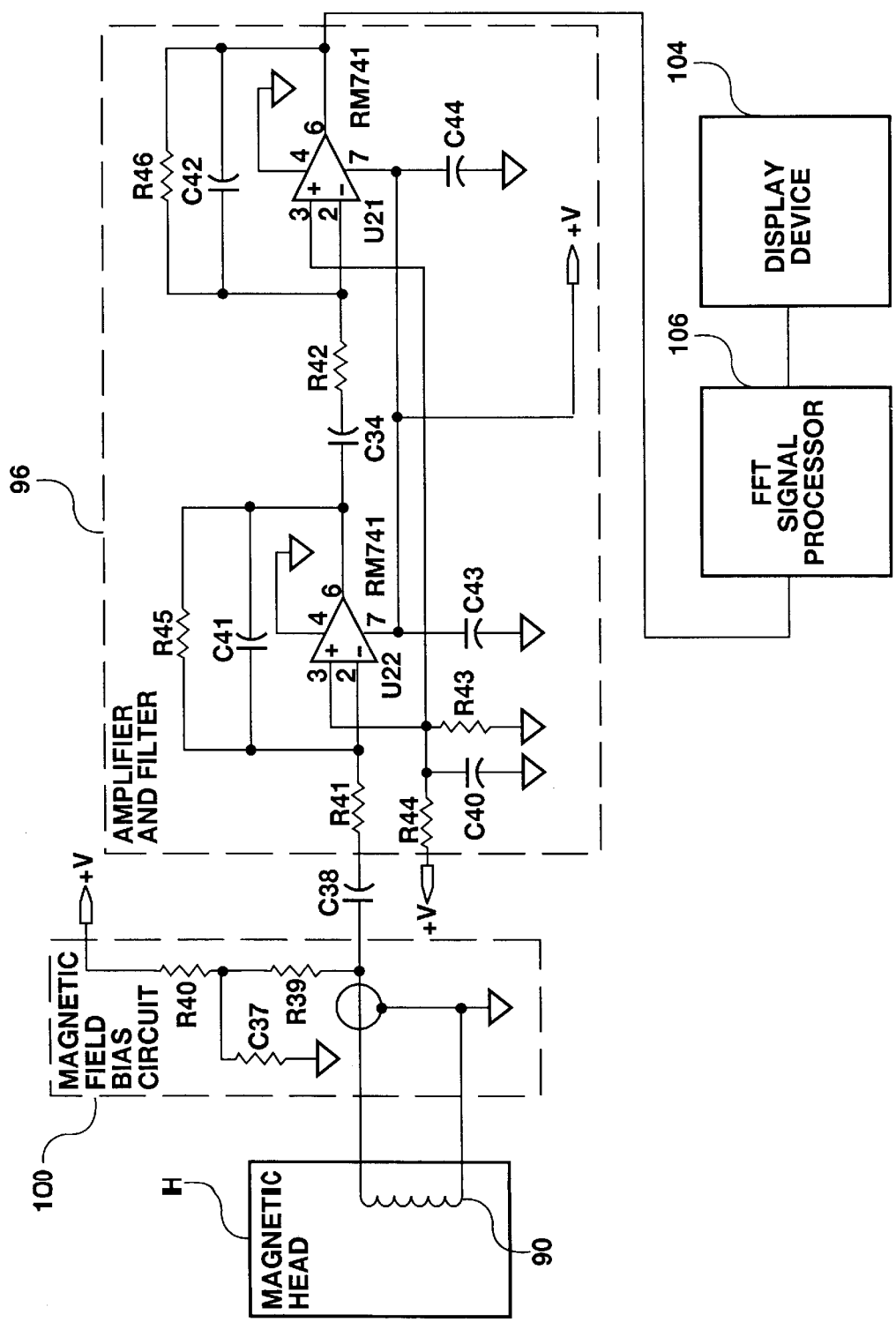
FIG. 15 is a hybrid block diagram and detailed circuit diagram of the device of FIG. 14.

FIG. 15 depicts detailed circuitry for the magnetic head circuit 98 and the amplifier and filter circuit 96 of FIG. 14. A magnetic field bias circuit 100 provides the DC current to the magnetic head coil 90 to generate the magnetic field. The values for resistors R39 and R40 are selected to provide the proper amount of current needed to generate an adequate magnetic field at the air-gap 92 (FIG. 14). Capacitor C37 provides a bias for the magnetic head current.

The signal generated in the magnetic head coil 90 is coupled through capacitor C38 to the amplifier and filter 96. Operational amplifier U22 and its associated resistors and capacitors filter out noise generated by the motor 80 and other sources. Capacitors C38 and C41 and resistors R41 and R45 are selected for a bandpass around the desired signal frequency—typically in the 400 to 500 Hertz range. Alternatively, a notch filter may be used to filter the noise. The amplifier uses two operational amplifier circuits to provide the necessary amplification—typically on the order of 1,000:1. The components associated with operational amplifier U21 are identical to the components associated with operational amplifier U22. Resistors R43 and R44 and capacitor C40 provide gain and bias for the two operational amplifier stages.

In FIG. 15, the signal processor 102 of FIG. 14 is replaced by an FFT signal processor 106. The FFT signal processor 106 provides additional noise reduction using "Fast Fourier Transform" signal processing. In practice, a null of greater than 100 DB can be obtained. Consequently, the use of the FFT signal processor 106 improves the sensitivity of the screening device. The operation and construction of FFT signal processors and associated noise reduction techniques are well-known and widely used in the signal processing art. Accordingly, these details will not be discussed further.

After the amplified and filtered signal is processed by either the FFT signal processor 106 of FIG. 15 or the signal processor 102 of FIG. 14, the processed signal drives a display device 104. The display device 104 generates a visual indication of the probability of whether the diamond sample is a synthetic diamond or a natural diamond.

The third embodiment typically provides a more sensitive screening device than the first and second embodiments. First, because an oscillator is not used, the sensitivity of the circuit is not affected by oscillator frequency drift. Second, the circuit does not rely on a change in a circuit parameter (e.g., inductance). Thus, the circuit is not affected by the errors produced by the circuitry that detects changes in circuit parameters. Third, the FFT processing improves the sensitivity of the circuit when detecting very small signals in the presence of noise. Tests have demonstrated that this embodiment exhibits surprising sensitivity (typically in the order of a 100 DB signal-to-noise ratio) and, as a result, can distinguish between a natural diamond and a synthetic diamond that contains very little ferrous material. Thus, this embodiment provides a very effective yet relatively simple method for distinguish between a synthetic diamond and a natural diamond.

From the above, it can be seen that the present invention provides a simple and accurate method of distinguishing between synthetic diamonds and natural diamonds.

While certain specific embodiments of the invention are disclosed as typical, the invention is not limited to these particular forms, but rather is applicable broadly to all such variations as fall within the scope of the appended claims. To those skilled in the art to which the invention pertains many modifications and adaptations will occur. For example, while the oscillators and other circuits shown have been implemented with discrete components, they could readily be implemented on a programmable logic chip or chips as well. A variety of circuits could be used to construct the oscillator, comparator, amplifier, filter and output circuits described above. The change in the effective inductance of a coil could be detected using various filter circuits or signal response circuits. Various audio or visual devices could be used to indicate whether the diamond sample is synthetic or natural. A variety of mechanisms could be used to move the diamond sample in the magnetic field. Similarly, a variety of magnetic head devices could generate the magnetic field and/or detect changes in the magnetic field. Thus, the specific structures discussed in detail above are merely illustrative of a few specific embodiments of the invention.

What is claimed is:

1. An apparatus for distinguishing between a synthetic diamond and a natural diamond by rotating a diamond sample in a magnetic field and detecting a signal generated by said rotating of said diamond sample in said magnetic field, comprising:

a magnetic field generator for producing a magnetic field;

a motor for rotating said diamond sample in said magnetic field;

a detector for detecting an alternating current signal generated by said rotating of said diamond sample in said magnetic field; and a signal processor for processing said alternating current signal to generate a second signal indicative of a probability of whether said diamond sample is a synthetic diamond or a natural diamond.

2. An apparatus according to claim 1 wherein said magnetic field generator and said detector are comprised, in part, of an air-gap magnetic head.

3. An apparatus according to claim 2 wherein said motor rotates at a speed in the range of approximately 25,000 to 30,000 revolutions per minute.

4. A method for distinguishing between a synthetic diamond and a natural diamond by rotating a diamond sample in a magnetic field and detecting a signal generated by said rotating of said diamond sample in said magnetic field, said method comprising the steps of:

generating a magnetic field;

rotating said diamond sample in said magnetic field;

detecting an alternating current signal generated by said rotating of said diamond sample in said magnetic field; and processing said alternating current signal to generate a second signal indicative of a probability of whether said diamond sample is a synthetic diamond or a natural diamond.

5. A method according to claim 4 wherein an air-gap magnetic head generates said magnetic field and detects said first signal.

6. A method according to claim 4 wherein said rotating is performed at a speed in the range of approximately 25,000 to 30,000 revolutions per minute.

7. A method according to claim 4 wherein said processing step further comprises the step of applying Fast Fourier Transform processing to said second signal.

8. An apparatus for distinguishing between a synthetic diamond and a natural diamond, the apparatus comprising:

a motor for inducing rotational motion between at least one diamond sample and at least one magnetic detector;

at least one magnetic detector for generating an alternating current signal, responsive to said motion; and a signal processor for generating a second signal indicative of a probability of whether said at least one diamond sample is a synthetic diamond or a natural diamond by sampling and processing said alternating current signal, as a means of improving sensitivity for determining said probability.

9. The apparatus of claim 8 wherein said sampling and processing comprise fast fourier transform operations.

10. The apparatus of claim 9 wherein said motion comprises rotation.

11. The apparatus of claim 10 wherein said magnetic detector comprises a magnetic field generator for generating a magnetic field and wherein said magnetic detector detects alteration of said magnetic field as caused by said motion.

12. The apparatus of claim 11 further comprising a display device for providing a visual indication of whether said at least one diamond sample is a synthetic diamond or a natural diamond, in accordance with said second signal.

13. A method for distinguishing between a synthetic diamond and a natural diamond, the method comprising the step of:

generating a magnetic field;

inducing rotational motion between a diamond sample and said magnetic field;

detecting an alteration of said magnetic field caused by said motion between said diamond sample and said magnetic field;

generating an alternating current signal in response to said detecting of an alteration of said magnetic field; and processing said alternating current signal to generate a second signal indicative of a probability of whether said diamond sample is a synthetic diamond or a natural diamond.

14. The method of claim 13 wherein said motion comprises rotation.

15. An apparatus for distinguishing between a synthetic diamond and a natural diamond, the apparatus comprising:

a magnetic field generator for generating a magnetic field;

a motor for inducing rotational motion between a diamond sample and said magnetic field;

a detector for detecting an alteration of said magnetic field caused by said motion between said diamond sample and said magnetic field;

a signal generator for generating an alternating current signal in response to said detecting of an alteration of said magnetic field; and a signal processor for processing said alternating current signal to generate a second signal indicative of a probability of whether said diamond sample is a synthetic diamond or a natural diamond.

16. The apparatus of claim 15 wherein said motion comprises rotation.

17. A method for processing an alternating current signal to distinguish between a synthetic diamond and a natural diamond, the method comprising the step of:

receiving an alternating current signal generated as a result of rotational motion between a diamond sample and a magnetic field;

processing said alternating current signal using fast fourier transforms to generate a second signal; and processing said second signal to generate a third signal indicative of a probability of whether said diamond sample is a synthetic diamond or a natural diamond.

18. The method of claim 17 further comprising the step of providing a visual indication of whether said diamond sample is a synthetic diamond or a natural diamond, in accordance with said third signal.

* * * * *